United States Patent [19] [11] Patent Number: 5,066,666
Ozato et al. [45] Date of Patent: Nov. 19, 1991

[54] AMINOAZOLE DERIVATIVES AND THEIR PRODUCTION AND USE

[75] Inventors: Yukinori Ozato, Takarazuka; Nobuhiko Tamura, Toyonaka; Hiroaki Masumori, Ibaraki; Michihiro Yamamoto, Nishinomiya; Atsuyuki Kojima, Takarazuka; Fumio Nishikaku, Itami; Yoshihiko Kimura, Osaka, all of Japan

[73] Assignee: Sumitomo Pharmaceuticals Company, Limited, Osaka, Japan

[21] Appl. No.: 470,731

[22] Filed: Jan. 26, 1990

Related U.S. Application Data

[62] Division of Ser. No. 55,079, May 28, 1987, Pat. No. 4,914,112.

[30] Foreign Application Priority Data

Jun. 3, 1986 [JP] Japan ............................... 61-128910
Jul. 11, 1986 [JP] Japan ............................... 61-164508

[51] Int. Cl.$^5$ ..................... C07D 261/14; C07D 31/42
[52] U.S. Cl. .................................. 514/380; 548/133; 548/181; 548/190; 548/196; 548/199; 548/234; 548/245; 548/246
[58] Field of Search .................... 548/245, 246; 84/380

[56] References Cited

U.S. PATENT DOCUMENTS

| 3,720,685 | 3/1973 | Brewer et al. | 514/380 |
| 4,150,143 | 4/1979 | Neville et al. | 514/380 |
| 4,261,994 | 4/1981 | Dimsdale | 514/380 |
| 4,269,978 | 5/1981 | Petipierre | 514/380 |
| 4,307,106 | 12/1981 | Lombardino | 514/380 |
| 4,336,264 | 6/1982 | Wickiser | 514/380 |

FOREIGN PATENT DOCUMENTS

| 0001727 | 6/1979 | European Pat. Off. |
| 0005091 | 10/1979 | European Pat. Off. |
| 0091726 | 10/1983 | European Pat. Off. |
| 0177463 | 4/1986 | European Pat. Off. |
| 1121052 | 7/1962 | Fed. Rep. of Germany |
| 2461882 | 7/1975 | Fed. Rep. of Germany |
| 5175 | 6/1967 | France |
| 2068418 | 8/1971 | France |
| 2100914 | 3/1972 | France |
| 2439192 | 5/1980 | France |
| 188625 | 12/1988 | Japan | 548/245 |
| 2084140 | 4/1982 | United Kingdom |

Primary Examiner—Robert Gerstl
Attorney, Agent, or Firm—Stevens, Davis, Miller & Mosher

[57] ABSTRACT compound of the formula:

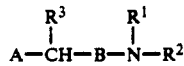

wherein A is the group of the formula:

$Ar^1-D-Ar^2-$ wherein $Ar^1$ is a phenyl or thienyl group which may be optionally substituted with at least one of the same or different halogen atom; $Ar^2$ is a phenylene or thienylene group which may be optionally substituted with at least one of the same or different halogen atom; D is a divalent radical selected from the group consisting of $>=N-OR^4$ [wherein $R^4$ is a hydrogen atom or lower alkyl group], $>C=O$,

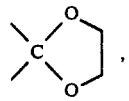

$>CHOH$, $>NH$ radical, or single bond,

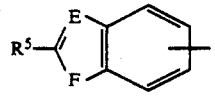

wherein $R^5$ is a lower alkoxy or a phenyl group which may be optionally substituted with at least one of the same or different halogen atom; E is a methine group or a nitrogen atom; F is a vinylene group or an oxygen atom,

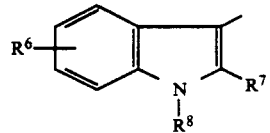

wherein $R^6$ is a lower alkoxy group; $R^7$ is a lower alkyl group; $R^8$ is a benzoyl group which may be optionally substituted with at least one of the same or different halogen atom, B is a divalent azole group;
$R^1$ is a hydrogen atom or a lower alkyl group;
$R^2$ is a hydrogen atom, lower alkyl aryl-lower alkyl, or the group of the formula:

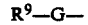

wherein $R^9$ is a hydrogen atom, lower alkyl, halo-lower alkyl, amino-lower alkyl, aryl or aryl-lower alkyl group or the group of the formula:

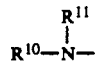

wherein $R^{10}$ is a hydrogen atom or lower alkyl group; $R^{11}$ is a hydrogen atom, lower alkyl, lower alkenyl, lower cycloalkyl, aryl-lower alkyl, aryl or aroyl group; or the group of the formula: $-NR^{10}R^{11}$ is a 5-, (Abstract continued on next page.)

6- or 7-membered saturated heterocyclic ring; or the group of the formula:

$$R^{12}-O-$$

wherein $R^{12}$ is a lower alkyl or polyhalo-lower alkyl group;

G is a divalent group selected from the group consisting of $>C=O$, $>C=S$, $>(C=O)_2$ or $>SO_2$ radical; or the group of the formula: $-NR^1R^2$ is a 5-, 6- or 7-membered saturated heterocyclic ring:

$R^3$ is a hydrogen atom or lower alkyl group, or its acid addition salts, which is useful for immunomodulator.

7 Claims, No Drawings

AMINOAZOLE DERIVATIVES AND THEIR PRODUCTION AND USE

This is a division of application Ser. No. 07/055,079, filed May 28, 1987, now Pat. No. 4,914,112.

This invention related to novel aminoazole derivatives useful as therapeutic and preventive agents of autoimmune diseases, for example, rheumatoid arthritis or systemic lupus erythematodes, inflammatory, allergy and asthma, and their production and use. More particularly, the novel compounds of this invention are those of the formula:

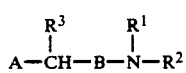 (I)

wherein A is the group of the formula:

wherein $Ar^1$ is a phenyl or thienyl group which may be optionally substituted with at least one of the same or different halogen atom; $Ar^2$ is a phenylene or thienylene group which may be optionally substituted with at least one of the same or different halogen atom; D is a divalent radical selected from the group consisting of $>C=N-OR^4$ [wherein $R^4$ is a hydrogen atom or lower alkyl group], $>C=O$,

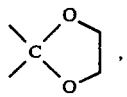

$>CHOH$, $>NH$ radical, or single bond,

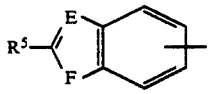

wherein $R^5$ is a lower alkoxy or a phenyl group which may be optionally substituted with at least one of the same or different halogen atom; E is a methine group or a nitrogen atom; F is a vinylene group or an oxygen atom,

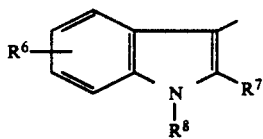

wherein $R^6$ is a lower alkoxy group; $R^7$ is a lower alkyl group; $R^8$ is a benzoyl group which may be optionally substituted with at least one of the same or different halogen atom, B is a divalent azole group;
$R^1$ is a hydrogen atom or a lower alkyl group;
$R^2$ is a hydrogen atom, lower alkyl, aryl-lower alkyl, or the group of the formula:

wherein $R^9$ is a hydrogen atom, lower alkyl, halolower alkyl, amino-lower alkyl, aryl or aryl-lower alkyl group or the group of the formula:

wherein $R^{10}$ is a hydrogen atom or lower alkyl group; $R^{11}$ is a hydrogen atom, lower alkyl, lower alkenyl, lower cycloalkyl, aryl-lower alkyl, aryl or aroyl group, the group of the formula: $-NR^{10}R^{11}$ is a 5-, 6-, 7-membered saturated heterocyclic ring, or the group of the formula:

wherein $R^{12}$ is a lower alkyl or polyhalo-lower alkyl group; G is a divalent group selected from the group consisting of $>C=O$, $>C=S$, $>(C=O)_2$ or $>SO_2$ radical; or the group of the formula: $-NR^1R^2$ is a 5-, 6- or 7-membered saturated heterocyclic ring; and $R^3$ is a hydrogen atom or lower alkyl group, and the pharmaceutically acceptable acid addition salts thereof.

Various compounds, such as steroids, non-steroidal anti-inflammatory drugs and gold compounds, etc., are now widely use in treatment of autoimmune diseases, for example, rheumatoid arthritis, but all of their drugs are limited use clinically because of their side effects in addition to unreliable clinical effects. As a result of the elucidations for the pathogenesis of autoimmune diseases, immunomodulators, which may alter the course of the diseases, have been used for the treatment of the diseases. As the immunomodulators, levamizole and D-penicillamine are described in the publications, Saishin Igaku, 35, 1392 (1980) and Igaku no Ayumi, 101, 216 (1977) respectively. However, they produce serious side effects, which cause a great problem in their clinical use.

It has been reported that aminoazoles have several biological activities. In recent years, 2-aminothiazoles such as fanetizole, 2-phenethylamino-4-phenylthiazole, (U.S. Pat. No. 4,307,106) and lotifazole, 4-phenyl-2-(2',2',2'-trichloroethoxycarboxamido)thiazole, (E.P. Pat. No. 1,727), which regulate immune responses, are reported.

In addition, 2-aminothiazole derivatives were described as gastric secretion inhibitor (E.P. Pat. No. 177,463). It was reported that 2-aminooxazole derivatives were effective for asthma (D.E. Pat. No. 2,459,380). It was reported that 5-aminoisoxazole derivatives were effective for convulsion and acute inframmation (F.R. Pat. No. 2,068,418). 3-Amino-1,2,4-oxadiazole derivatives were described as hypotensive drug (F.R. Pat. No. 2,439,192), and as carrageeninedema inhibitor (D.E. Pat. No. 2,124,907).

It has been hoped that therapeutic agents of rheumatoid arsthritis are effective for chronic inflammation and active as regulants of the immune response in the body. Rat-adjuvant arthritis test is useful as pharmacological model to examine effects for chronic inflammation, and mice-Arthus reaction is useful as pharmacological model to examine the immune regulant activity.

D-penicillamine is non-effective for adjuvant arthritis test and arthus reaction, moreover, has many severe side-effects. Levamizole is effective for Arthus reaction, however, is non-effective for adjuvant arthritis test and has many severe side-effects. Fanetizole and lotifazole are effective for Arthus reaction, however, are non-effective for adjuvant arthritis test.

Accordingly, for the therapeutic agent of rheumatoid arthritis have been desired the compounds which is effective for both of adjuvant arthritis test and Arthus reaction, and furthermore, have less side effect.

As the result of an extensive study, it has now been found that the aminoazole derivatives (I) of the invention exhibit depressive activities for both adjuvant arthrisis and Arthus reaction, in addition to inhibitory activity of 5-lipoxygenase. Therefore, the aminoazoles (I) are useful for treatment of autoimmune diseases, e.g. rheumatoid arthritis, systemic lupus erythematodes inflammatory, allergy, asthma e.t.c. This invention is based on the above finding.

Accordingly, a main object of the invention is to provide the aminoazoles (I) and their pharmaceutically acceptable acid addition salts. Another object of this invention is to provide processes for production of the aminoazoles (I). A further object of the invention is to provide use of the aminoazoles (I) as immunomodulators or anti-inflammatory drugs.

In the compounds of the above formula (I) and elsewhere in the specification, the terms "alkyl" and "alkenyl" means both straight and branched-$C_{1-4}$ hydrocarbon chains, and the lower alkyl may be $C_{1-4}$ alkyl such as methyl, ethyl, n-propyl, isopropyl, n-butyl, isobutyl, sec-butyl, tert-butyl. The lower alkenyl may be $C_{2-4}$ alkenyl such as vinyl, allyl, n-propenyl, isopropenyl, 2-methyl-1-propenyl, 1- or 2- or 3-butenyl and the like. The lower alkoxy may be $C_{1-4}$ alkoxy such as methoxy, ethoxy, n-propoxy, isopropoxy, n-butoxy and the like. The halo-lower alkyl may be halo($C_{1-4}$)alkyl such as chloromethyl, bromomethyl, 1-chloroethyl, 2-chloroethyl, 1-bromoethyl, 2-bromoethyl, 1-chloropropyl, 2-chloropropyl, 3-chloropropyl and the like. The polyhalo-lower alkyl may be polyhalo($C_{1-4}$)alkyl such as trifluoromethyl, trichloromethyl, 2,2,2-trifluoroethyl, 2,2,2-trichloroethyl and the like. The amino-lower alkyl may be amino($C_{1-4}$)alkyl such as aminomethyl, 2-aminoethyl, 3-aminopropyl, 2-(N-methylamino)ethyl, 2-(N,N-dimethylamino)ethyl. The lower cycloalkyl may be $C_{3-6}$ alicyclic group such as cyclopropyl, cyclobutyl, cyclopentyl, cyclohexyl and the like. The aryl may be a phenyl group which may be optionally substituted with the lower alkyl group, such as phenyl, 4-methylphenyl, 4-ethylphenyl and 4-isopropylphenyl and the like. The aryl-lower alkyl may be phenyl($C_{1-4}$)alkyl such as benzyl, phenethyl, phenylpropyl. The substituted benzoyl may be a benzoyl group substituted with at least one of the same or different halogen atom, e.g., 4-chlorobenzoyl, 4-fluorobenzoyl, 2-chlorobenzoyl, 2-fluorobenzoyl. The aroyl may be benzoyl or benzoyl group substituted with at least one of the same or different halogen atom, or of the same or different lower alkyl group, e.g., 4-chlorobenzoyl, 4-fluorobenzoyl, 4-methylbenzoyl. The term "halogen" includes, fluorine, chlorine, bromine and iodine. The 5-, 6-, 7-membered saturated heterocyclic ring may, for example, be pyrrolidinyl, pipelidinyl, hexahydroazepinyl. The azole group is a 5-membered heterocyclic ring having one nitrogen atom and further at least one selected from the group consisting of oxygen, sulfur and nitrogen atom, such as, thiazole, oxazole, isoxazole, oxadiazole, isothiazole, thiadiazole, pyrazole, imidazole, triazole and the like.

Among the amino azole compounds (I) of the invention, those of the following formula are preferable:

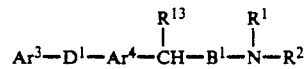

wherein $Ar^3$ is a phenyl group which may be optionally substituted with at least one of the same or different halogen atom; $Ar^4$ is a phenylene group which may be optionally substituted with at least one of the same or different halogen atom; $D^1$ is carbonyl group or single bond; $B^1$ is the divalent azole group of thiazolediyl, oxazolediyl, isoxazolediyl or oxadiazolediyl; $R^{13}$ is lower alkyl group; $R^1$ and $R^2$ are as defined above and the pharmaceutically acceptable acid addition salts.

The compounds of the formula are more preferable:

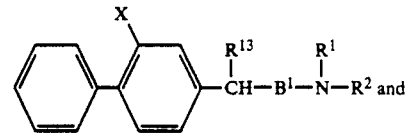

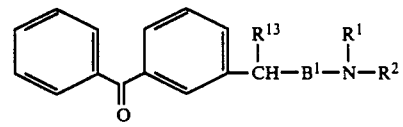

wherein X is hydrogen or halogen atom; $B^1$, $R^1$, $R^2$, $R^{13}$ are as defined above and the pharmaceutically acceptable acid addition salts.

The compounds of the formula are most preferable:

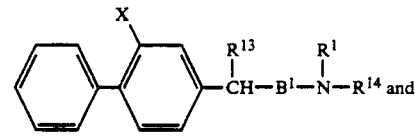

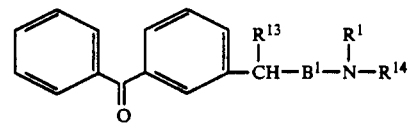

wherein $R^{14}$ is hydrogen atom or lower alkyl group; X, $B^1$, $R^1$, $R^2$ are as defined above and the pharmaceutically acceptable acid addition salts.

The pharmaceutically acceptable acid addition salts of the novel aminoazole derivatives are also embraced by the present invention and are readily prepared by contacting the free base with the appropriate mineral or organic acid in either aqueous solution or in a suitable organic solvent. The solid salt may then be obtained by precipitation or by evaporation of the solvent. The pharmaceutically acceptable acid addition salts of this invention include, but are not limited to, the hydrochloride, hydrobromide, sulfate, phosphate, formate, acetate, fumarate, maleate, malate, tartrate, aspartate, glutamate, methanesulfonate, benzenesulfonate, p-toluenesulfonate, hydroxybenzenesulfonate, dihydroxybenzenesulfonate, and the like. The compounds of this invention include optical isomers, tautomers, all of hydrates and those crystal forms.

The amino azole compounds (I) can be produced by various processes, of which typical examples are set forth below.

PROCESS (A)

The process of the azole (I) comprises cyclization:
The cyclization processes comprise the following five procedures:

Procedure 1

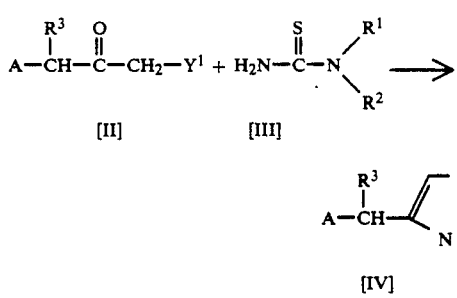

wherein $Y^1$ is a leaving group such as halogen (e.g. chlorine, bromine), alkylsulfonyloxy (e.g. methanesulfonyloxy) or arylsulfonyloxy (e.g. p-toluenesulfonyloxy), and A, $R^1$, $R^2$ and $R^3$ are as defined above.

The compound (IV) is obtained by reacting the compound (II) with the compound (III) in an inert solvent at room temperature or under heating. As the solvent there may be used water, alcohols (e.g. methanol, ethanol), ethers (e.g. ethyl ether or tetrahydrofuran), haloalkanes (e.g. dichlorometane, chloroform) or their mixture.

Procedure 2

$$A-\overset{R^3}{\underset{|}{CH}}-\overset{O}{\underset{\|}{C}}-CH_2-OH + H_2NCN \longrightarrow$$

[V]

(structure [VI] with NH₂)

wherein A and $R^3$ are as defined above.

The compound (VI) is obtained by reacting the compound (V) with cyanamide in an inert solvent at room temperature or under heating in the presence of the base such as sodium hydroxide, potassium hydroxide, sodium carbonate or potassium carbonate. As the solvent, there may be used alcohols (e.g. methanol, ethanol), ethers (e.g. tetrahydrofuran, 1,4-dioxane), water or their mixture.

Procedure 3

$$A-\overset{R^3}{\underset{|}{CH}}-\overset{O}{\underset{\|}{C}}-CH_2CN + HONH_2 \longrightarrow$$

[VII]

(structure [VIII] with NH₂)

wherein A and $R^3$ are as defined above.

The compound (VIII) is obtained by reacting the compound (VII) with hydroxylamine in an inert solvent at room temperature or under heating. As the solvent, there may be used alcohols (e.g. methanol, ethanol), aromatic hydrocarbons (e.g. benzen, toluen), haloalkanes (e.g. dichloromethane, chloroform), ethers (e.g. tetrahydrofurane, 1,4-dioxane), N,N-dimethylformamide, N,N-dimethylacetamide or pyridine. In case using hydroxylamine-acid salts, the reaction in presence of the acid binding agent may be effective. As the acid-binding agent, there may be used an inorganic base or organic base, of which example are sodium hydroxide, potassium hydroxide, sodium carbonate, sodium bicarbonate, triethylamine or pyridine.

Procedure 4

(scheme IX + X → XII → XI)

wherein A, $R^1$, $R^2$ and $R^3$ are as defined above.

The compound (XI) is obtained by reacting the compound (IX) or its reactive ester with the compound (X) in an inert solvent at room temperature or under heating. As the solvent, there may be used aromatic hydrocarbons (e.g. benzene, toluene), haloalkanes (e.g. dichloromethane, chloroform), ethers (e.g. tetrahydrofuran, 1,4-dioxane), N,N-dimethylformamide, N,N-dimethylacetamide or pyridine. As the reactive ester of the compound (IX), there may be used a carboxylic acid halide (e.g. chloride, bromide, iodide), carboxylic anhydride including a mixed anhydride, a carboxylic azide or an active ester such as 4-acyloxy-2,3-dihydro-2,5-diphenyl-3-oxothiophene-1,1-dioxide. The free acid may be reacted in presence of N,N-dicyclohexylcarbodiimide(DCC), 1-hydroxybenztriazole (HOBT)-DCC, N,N-carbonyldiimidazole or 1-ethyl-3-(3-dimethylaminopropyl)carbodiimide hydrochloride (WSC.HCl). The acid chloride or anhydride may be preferably reacted in the presence of the acid-binding agent (e.g. sodium hydroxide, potassium hydroxide, sodium carbonate, potassium carbonate, triethylamine or pyridine). In case the intermediate (XII) is isolated in this reaction, it can be converted to the compound (XI) via intermolecular cyclization followed by dehydration with further heating in the presence or absence of an inert solvent.

Procedure 5

[XIII]

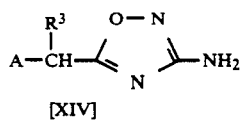
[XIV]

wherein A and $R^3$ are as defined above.

The compound (XIV) is obtained by reacting the compound (XIII) with hydroxylamine in an inert solvent at room temperature or under heating. As the solvent, there may be used aromatic hydrocarbons (e.g. benzene, toluene), ethers (e.g. tetrahydrofuran, 1,4-dioxane), N,N-dimethylformamide, N,N-dimethylacetamide or pyridine. In case using hydroxylamine-acid salts, the reaction in presence of the acid binding agent may be effective. As the acid-binding agent, there may be used an inorganic base or organic base, of which example are sodium hydroxide, potassium hydroxide, sodium carbonate, sodium bicarbonate, triethylamine or pyridine.

PROCESS (B)

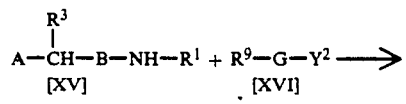

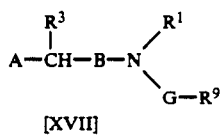
[XVII]

wherein $Y^2$ is a leaving group such as halogen (e.g. chlorine, bromine), alkylsulfonyloxy (e.g. methanesulfonyloxy) or arylsulfonyloxy (e.g. p-toluenesulfonyloxy), and A, B, G, $R^1$, $R^3$ and $R^9$ are as defined above.

The compound (XVII) is obtained by reacting the compound (XV) with the compound (XVI) in an inert solvent in the presence of acid-binding agent at the condition from ice-cooling to heating. As the solvent, there may be used aromatic hydrocarbons (e.g. benzene, toluene), haloalkanes (e.g. dichloromethane, chloroform), ethers (e.g. tetrahydrofuran, 1,4-dioxane), N,N-dimethylformamide, N,N-dimethylacetamide or acetone. As the acid-binding agent, there may be used an inorganic base or organic base, of which example are sodium hydroxide, potassium hydroxide, sodium carbonate, sodium bicarbonate, triethylamine or pyridine. In case the reaction is performed under two-phase condition, use of phase-transfer catalysis may be effective.

PROCESS (C)

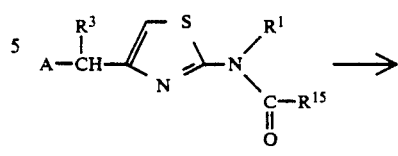
[XVIII]

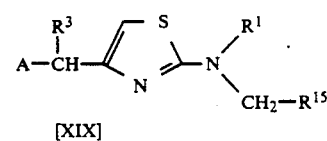
[XIX]

wherein $R^{15}$ is lower alkyl, aryl-lower alkyl or aryl and A, $R^1$ and $R^3$ are as defined above.

The compound (XIX) is obtained by reducing the compound (XVIII) with metal hydride such as lithium aluminium hydride at a temperature from cooling to under heating. As the solvent, there may be used ethyl ethers (e.g. ether tetrahydrofuran).

PROCESS (D)

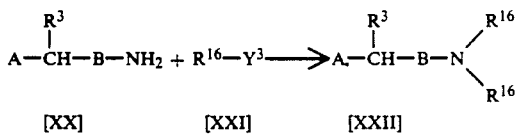
[XX]   [XXI]   [XXII]

wherein $R^{16}$ is lower alkyl or aryl-lower alkyl; $Y^3$ is a leaving group such as halogen (e.g. chlorine, bromine), alkylsulfonyloxy (e.g. methanesulfonyloxy) or arylsulfonyloxy (e.g. p-toluenesulfonyloxy) and, A, B and $R^3$ are as defined above.

The compound (XXII) is obtained by reacting the compound (XX) with the compound (XXI) in an inert solvent at a temperature from cooling to heating. As the solvent, there may be preferably used solvents combined hydrophobic solvent such as benzene or toluene with aqueous solution of strong base. Preferably this reaction is performed at room temperature. As the base, there may be used sodium hydroxide, potassium hydroxide or potassium carbonate.

PROCESS (E)

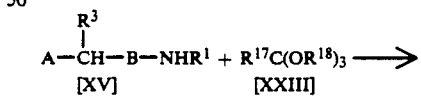
[XV]   [XXIII]

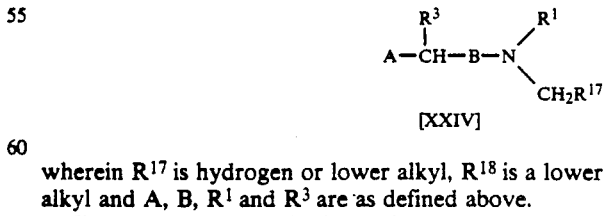
[XXIV]

wherein $R^{17}$ is hydrogen or lower alkyl, $R^{18}$ is a lower alkyl and A, B, $R^1$ and $R^3$ are as defined above.

The compound (XXIV) is obtained by reacting the compound (XV) with the compound (XXIII) under heating and then reducing with sodium borohydride in an inert solvent. As the solvent, there may be used alcohols (e.g. ethanol, propanol, isopropanol) or ethers (e.g. ethyl ether, tetrahydrofuran, 1,4-dioxane).

PROCESS (F)

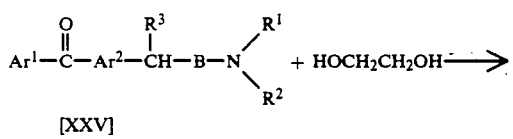

[XXV]

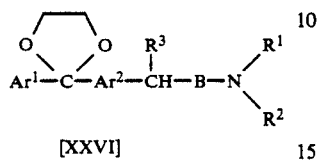

[XXVI]

wherein $Ar^1$, $Ar^2$, B, $R^1$, $R^2$ and $R^3$ are as defined above.

The compound (XXVI) is obtained by treating of the compound (XXV) with ethyleneglycol under the usual manner (for example "Shin-Jikkenkagaku Kouza" 14, (V), p. 2518, edited by NIHON-KAGAKUKAI). For example, the compound (XXVI) is obtained by heating the compound (XXV) with ethyleneglycol in aromatic hydrocarbons (e.g. benzene, toluene) in presence of p-toluenesulfonic acid.

PROCESS (G)

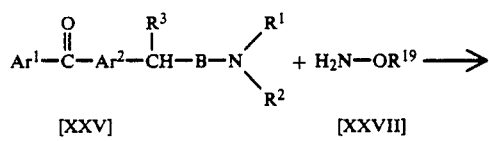

[XXV]    [XXVII]

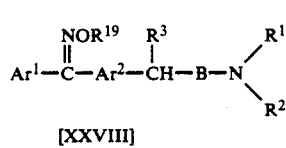

[XXVIII]

wherein $R^{19}$ is a hydrogen atom or lower alkyl and $Ar^1$, $Ar^2$, B, $R^1$, $R^2$ and $R^3$ are as defined above.

The compound (XXVIII) is obtained by reacting the compound (XXV) with the compound (XXVII) in an inert solvent at room temperature or under heating. As the solvent, there may be used alcohols (e.g. methanol, ethanol, propanol, isopropanol), ethers (e.g. tetrahydrofuran, 1,4-dioxane), aromatic hydrocarbons (e.g. benzene, toluene), pyridine or water. This reaction is performed by using of hydroxylamine-acid salts with an acid-binding agent such as sodium hydroxide, potassium hydroxide, sodium carbonate, potassium carbonate, sodium bicarbonate, triethylamine or pyridine.

PROCESS (H)

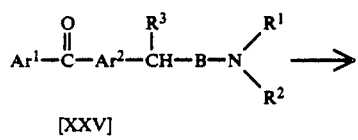

[XXV]

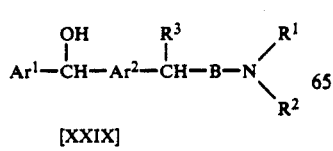

[XXIX]

wherein $Ar^1$, $Ar^2$, B, $R^1$, $R^2$ and $R^3$ are as defined above.

The compound (XXIX) is obtained by reducing the compound (XXV) with reducing agents such as sodium borohydride in an inert solvent at a temperature from ice-cooling to heating. As the solvent, there may be used alcohols (e.g. ethanol, n-propanol, isopropanol) or ethers (e.g. tetrahydrofuran, ethyl ether, 1,4-dioxane).

PROCESS (I)

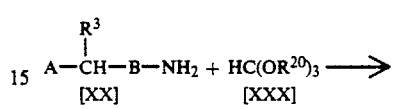

[XX]    [XXX]

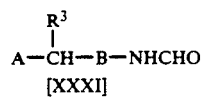

[XXXI]

wherein $R^{20}$ is lower alkyl, and A, B and $R^3$ are as defined above.

The compound (XXXI) is obtained by reacting the compound (XX) with the compound (XXX) under heating, followed by hydrolyzing under acid catalyst in an inert solvent. As the solvent, there may be used alcohols (e.g. methanol, ethanol, n-propanol, isopropanol), aromatic hydrocarbons (e.g. benzene, toluene), aliphatic hydrocarbons (e.g. hexane, heptane), haloalkanes (e.g. dichlorometane, chloroform), ethyl ether or their mixture. As the acid catalyst, there may be used mineral acid (e.g. hydrochloric acid, sulfuric acid) or silica-gel.

PROCESS (J)

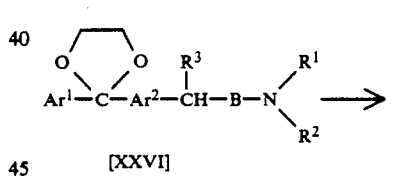

[XXVI]

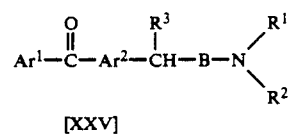

[XXV]

wherein $Ar^1$, $Ar^2$, B, $R^1$, $R^2$ and $R^3$ are as defined above.

The compound (XXV) is obtained by hydrolysis of the compound (XXVI) by usual manner (for example, Sin-Jikkenkagaku-Kooza 14, (V), p2519, edited by NI-HON-KAGAKUKI). For example, the compound (XXV) is obtained by reacting the compound (XXVI) with 80% acetic acid at room temperature.

PROCESS (K)

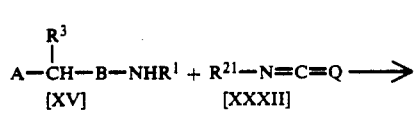

[XV]    [XXXII]

-continued

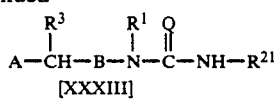
[XXXIII]

wherein O is oxygen or sulfer atom, $R^{21}$ is lower alkyl, lower alkenyl, lower cycloalkyl, aryl-lower alkyl, aryl or aroyl group, and A, B, $R^1$ and $R^3$ are as defined above.

The compound (XXXIII) is obtained by reacting the compound (XV) with the compound (XXXII) in an inert solvent at a temperature or under ice-cooling or heating. As the solvent, there may be used alcohols (e.g. methanol, ethanol), aromatic hydrocarbons (e.g. benzene, toluene), ethers (e.g. tetrahydrofuran, 1,4-dioxane), haloalkane (e.g. dichloromethane, chloroform), N,N-dimethylformamide, N,N-dimethylacetamide or acetone. This reaction is preferably performed in presence of an inorganic base (e.g. sodium carbonate, potassium carbonate, sodium bicarbonate). If necessary, this reaction is performed after the amines (XV) was converted to metal amide with metalating agent such as lithum diisopropylamide.

PROCESS (L)

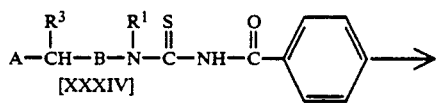
[XXXIV]

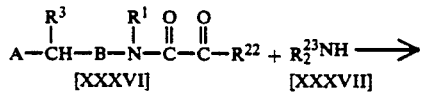
[XXXV]

wherein A, B, $R^1$ and $R^3$ are as defined above.

The compound (XXXV) is obtained by hydrolysis of the compound (XXXIV) in an inert solvent in presence of base under heating. As the solvent, there may be use alcohols (e.g. methanol, ethanol), ethers (e.g. tetrahydrofuran, 1,4-dioxane), acetone, water or their mixture. As the base, there may be used sodium hydroxide, potassium hydroxide, sodium carbonate, potassium carbonate, sodium bicarbonate.

PROCESS (M)

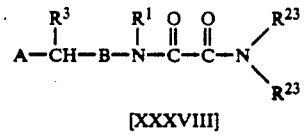
[XXXVI]  [XXXVII]

$$\begin{array}{c} R^3 \quad R^1 \quad O \quad O \quad R^{23} \\ | \quad | \quad \| \quad \| \quad / \\ A-CH-B-N-C-C-N \\ \quad \quad \quad \quad \quad \quad \quad \quad \quad \backslash R^{23} \end{array}$$
[XXXVIII]

wherein $R^{22}$ is halogen atom (e.g. chlorine, bromine) or lower alkyl group; $R^{23}$ is a hydrogen atom, lower alkyl group or $-NR_2^{23}$ is a 5-, 6-, 7-membered saturated heterocyclic ring, and A, B, $R^1$ and $R^3$ are as defined above.

The compound (XXXVIII) is obtained by reacting the compound (XXXVI) with the compound (XXXVII) in an inert solvent under heating. As the solvent, there may be used aromatic hydrocarbons (e.g. benzene, toluene), ethers (e.g. tetrahydrofuran, 1,4-dioxane), haloalkanes (e.g. dichloromethane, chloroform) or pyridine.

PROCESS (N)

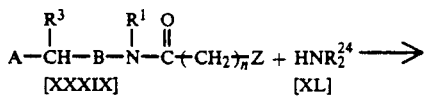
[XXXIX]  [XL]

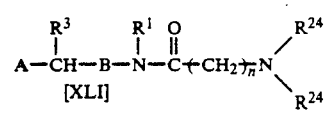
[XLI]

wherein Z is halogen (e.g. chlorine, bromine, iodine), $R^{24}$ is a hydrogen atom and lower alkyl, n is integer from 1 to 4, and A, B, $R^1$ and $R^3$ are as defined above.

The compound (XLI) is obtained by reacting the compound (XXXIX) with the compound (XL) in an inert solvent. As the solvent, there may be used aromatic hydrocarbons (e.g. benzene, toluene), ethers (e.g. tetrahydrofuran, 1,4-dioxane), haloalkanes (e.g. dichloromethane, chloroform), N,N-dimethylformamide, N,N-dimethylacetamide or pyridine. This reaction is effectively performed in the presence of an inorganic or an organic base (e.g. sodium hydroxide, potassium hydroxide, sodium carbonate, potassium carbonate, sodium bicarbonate, triethylamine or pyridine) at a temperature from ice-cooling or to heating.

PROCESS (P)

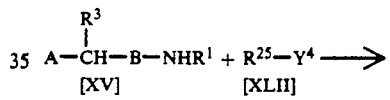
[XV]  [XLII]

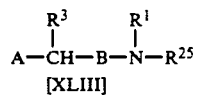
[XLIII]

wherein $R^{25}$ is lower alkyl or aryl-lower alkyl; $Y^4$ is a leaving group such as halogen (e.g. chlorine, bromine), alkylsulfonyloxy (e.g. methanesulfonyloxy) or arylsulfonyloxy (e.g. p-toluenesulfonyloxy), and A, B, $R^1$ and $R^3$ are as defined above.

The compound (XLIII) is obtained by reacting the compound (XV) with the compound (XLII) in an inert solvent in presence of the phase-transfer catalyst in addition to base. As the solvent, there may be used the mixture of hydrophobic solvents (e.g. benzene, toluene) and water. As the base, there may be used sodium hydroxide, potassium hydroxide or potassium carbonate.

The starting compounds (XV), (XVIII), (XX), (XXV), (XXXIV), and (XXXIX) are objective compounds of this invention and obtained by process (A-1), (A-2), (A-3), (A-4), (A-5), (B), (C), (E), (F), (J), (K) and (P). And the compounds (II), (III), (V), (VII), (IX), (X), (XIII), (XVI), (XXI), (XXIII), (XXVII), (XXX), (XXXII), (XXXVII) and (XLI) are known or obtained by usual manner. For example, the compound (II) and (V) are prepared by following process.

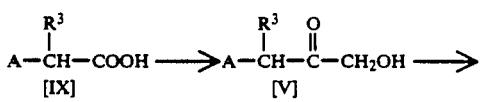
[IX]  [V]

-continued

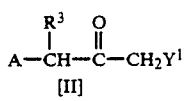

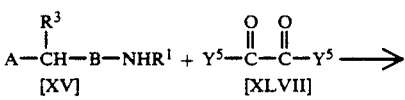

wherein A, $Y^1$, and $R^3$ are as defined above.

The compound (V) is prepared by reacting the acid chloride of the compound (IX) with tris(trimethylsilyloxy) ethylene according to the procedure reported in literature (for example, A. Wissner, J. Org. Chem. 44, (25) 4617 (1979)). The compound (II) is prepared from the compound (V) by the usual manner. For example, the compound (II) (wherein $Y^1$ is chlorine) is obtained by substitution of hydroxy group to chlorine atom with triphenylphosphinecarbon tetrachloride system.

The compound (XII) is prepared by the following procedure.

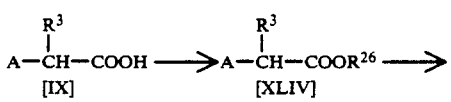

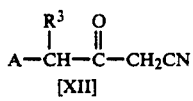

wherein $R^{26}$ is lower alkyl and A and $R^3$ are as defined above.

The compound (XLIV) is obtained by esterification of the compound (IX) by usual manner and the compound (VII) is obtained by base-catalytic condensation of the compound (XLIV) with acetonitrile.

The compound (XIII) is prepared by reacting the compound (IX) with cyanamide in an inert solvent at room temperature or under heating according to the procedure reported in D.E. Pat. No. 2,843,887.

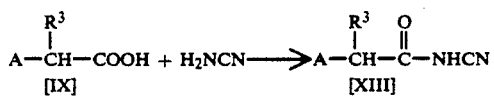

The starting compound (X) is known or obtained by following process.

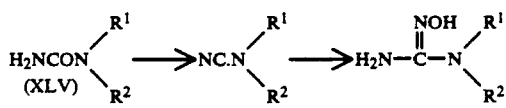

wherein $R^1$ and $R^2$ are as defined above.

The compound (XLVI) is obtained by dehydrating the compound (XLV) according to procedure reported in literature (for example, W. Schroth et al, Journal f. prakt, chemie, Band 325, Heft5, 1983, s 787-802).

The compound (X) is obtained by reacting the compound (XLVI) with hydroxylamine according to the procedure reported in literature (BEtZECKI et al, Bull, Acad. Pol. Sci. Ser Sci, Chem., vol 18, No. 8,431 (1970)).

The compound (XXXVI) is obtained by following process; when $R^{22}$ is a halogen atom, the compound (XLVII) is prepared by reacting the compound (XV) with the compound (XLVII) in inert solvent at room temperature or under heating.

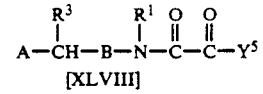

wherein $Y^5$ is a halogen atom (e.g. chlorine, bromine), and A, B, $R^1$ and $R^3$ are as defined above. When $R^{22}$ is lower alkoxy group, the compound (XXXVI) is obtained by process (B).

As stated above, the aminozoles (I) of this invention exert pharmaceutical activities to autoimmune diseases especially. The facts are well evidenced by the pharmacological test data as set forth below.

TEST METHOD

Rat-Adjuvant Arthritis Test

Rat adjuvant arthritis test is one of a few and most useful pharmacological model for the investigation of human clonic inflammation. It is known that the effective compounds to this model system are useful for treatment of rheumatoid arthritis, such as steroids or non-steroidal anti-inflammatory drugs (Oyo Yakuri, 5, 169 (1971)).

According to the method of Winter et al., Arth. Rheum., 9, 394 (1966), male Sprague-Dawley rats, 6 weeks of age, were given subplantar injection of the adjuvant consisting of 1 mg of killed *Mycobacterium butyricum* (Difco) and 0.2 ml of liquid paraffin. Fourteen days after, the rats with established arthritis were treated by the drug as follows: the test compound was suspended in 5% gum arabic solution and orally given once a day for 5 days, day 15 to day 19. Control rats were given gum arabic in the same way. On day 19, the volume of right foot was determined with a plethusometer. The lowest dose which gave significant reduction ($p<0.001$) of the foot volume from that of the control group was regarded as a minimum effective dose (MED).

Mice-Arthus Test

It's thought that rheumatoid arthritis is a disease with disorder of immunity and one of origins of this disease is Arthus reaction induced by immune complex (Ivan M. Roitt, 1980, "Essential Immunology"). The activity of effect for rheumatoid arthritis may be estimated by effect for Arthus reaction.

According to the method of Abe et al., Enshou, 1, 739 (1981), male BABL/c mice, 6 weeks of age, were sensitized by injection of $8 \times 10^7$ sheep red blood cells (SRBC) (Nihor. Bio-Sap. Center) in 0.2 ml of phosphate buffered saline (PBS) into the tail vein. Two weeks later, mice were boosted by the i.v. injection of $8 \times 10^7$ SRBC and 5 day later the animals were challenged by the subcutaneous injection of $1 \times 10^8$ SRBC in 25 μl of PBS into the right hind footpad. The thickness of the SRBC-injection right hind paw and contralateral left hind paw were measured with micrometer 3 hr after the challenge. The difference between these two measurements is regarded as the oedema due to the Arthus reaction. Percentage inhibition of the reaction was determined by comparison with the positive control group. The test compounds were administered orally 24 hr and 1 hr before the challenge. Results of two tests for compounds of example 2, 7, 9, 11, 21, 22, 48, 67, 74 are shown in Table 1.

TABLE 1

Results of Rat-Adjuvant Arthrits Test and Mice-Arthus Test

| Example No. | Structure | Minimum Effective Dose (mg/kg) | |
|---|---|---|---|
| | | Adjuvant Arthritis | Arthus |
| 2 | [structure] | 25 | 10 |
| 7 | [structure] | 10 | 10 |
| 9 | [structure] | 10 | 50 |
| 11 | [structure] | 2.5 | 10 |
| 21 | [structure] | 2.5 | 10 |
| 22 | [structure] | 2.5 | 50 |
| 48 | [structure] | 10 | 50 |
| 67 | [structure] | 10 | 50 |
| 74 | [structure] | 2.5 | 50 |
| | levamizole | non-effective at 50 mg/kg | 50 |

TABLE 1-continued

Results of Rat-Adjuvant Arthrits Test and Mice-Arthus Test

| Example No. | Structure | Minimum Effective Dose (mg/kg) | |
|---|---|---|---|
| | | Adjuvant Arthritis | Arthus |
| | D-Penicillamine | non-effective at 200 mg/kg | non-effective at 50 mg/kg |

The compounds of this invention are effective for both rat adjuvant arthritis test and mice Arthus reaction test, on the other hand, levamizole is non-effective for rat adjuvant arthritis and D-penicillamine is non-effective for both rat adjuvant arthritis and mice Arthus reaction. Therefore, the compounds of this invention are useful therapeutic agents of rheumatoid arthritis. That is to say, it is characteristic in that the compounds of this invention are effective for the treatment of not only rheumatoid arthritis but also disorder of immunity.

In addition, the compounds of this invention are effective to improve several immunological factors of spontaneous autoimmune disease animal: MRL/1 mice. The results obtained suggest a potential role for the compounds of this invention in the treatment of autoimmune disease in human, e.g. rheumatoid arthritis.

Additionally, the compounds of this invention are effective as 5-lipoxygenase inhibitor as set forth below.

TEST METHOD

5-Lypoxygenase Inhibitory Test

According to the method of Harvey et al., J. Pharmacol. Meth., 9, 147-155 (1983), polymorphonuclear leukocytes (PMNs) from Hartley guinea pigs weighting 280 to 350 g were elicited by intraperit oneal injection of 2% casein suspension (10 ml/100 g guiner pig weight), and collected 16-18 hrs later. The cells were washed with saline and finally suspended at $2.39 \times 10^7$ cells/ml in Krebs Ringer Bicarbonate buffer (KBR) pH 7.4.

935 μl of PMNs were aliquoted into 15 ml glass tubes and prewarmed to 37° C. in a shaking water bath. Drugs (10 μl of dimethylsulfoxide (DMSO)) were added 10 minutes prior to the addition of 1-$^{14}$C-arachidonic acid (New England Neuclear Co.; 50 μl of 2 μCi/mlKBR) and calciumionophor, A23187 (Calbiochem Boehring Co.; 5 μl of 1 mg/mlDMSO). The reaction was terminated after a further 10 min by the addition of 0.2M citric acid (100 μl). Unstimulated controls were also included to determine the increased metabolism of arachidonic acid due to A23187. Samples were diluted with water (4 ml) and extracted twice with ethyl acetate (5 ml). The ethyl acetate was concentrated under a stream of nitrogen and two-thirds of the residue was applied to TLC plates. The plates were developed in toluene:dioxane:acetic acid=65:34:1.5 at 10° C.

Radiochromatographic analysis of the labelled metabolites of [$^{14}$C] arachidonic acid utilized a Berthold LB283 TLC Linear Analyzer. In samples and controls, a ratio of radioactivity of 5-HETE in metabolites to all of metabolites of [$^{14}$C] arachidonic acid was calculated, and results were determined as percent inhibition calculated from those retios.

$$\text{Inhibition (\%)} = \frac{\text{Ratio of radioactivity of control} - \text{Ratio of radioactivity of sample}}{\text{Ratio of radioactivity of control}} \times 100$$

| Inhibition (%) | |
|---|---|
| <20% | − |
| 20-40% | + |
| 40-70% | ++ |
| 70%< | +++ |

Results of 5-lipoxygenase inhibition for compounds of example 21, 22, 65 and 67 are shown in Table 2.

TABLE 2

| Results of 5-Lipoxygenase Inhibitory Test | |
|---|---|
| Example No. | Activity of Inhibition |
| 21 | ++ |
| 22 | +++ |
| 65 | +++ |
| 67 | +++ |

From the above results, the compounds of this invention possess 5-lipoxygenase inhibitory activity and, therefore, they may be useful for treatment of allergy and inflammation, e.g. allergic asthma and allergic rhinitis.

The compounds (I) of present inve-tion may be used in the form of pharmaceutical composition adapted for enteral or parenteral administration. Accordingly, by conventional routes, for oral administration the compounds may be combined with a suitable solid or liquid carrier or diluent to form tablets, capsules, powders, syrups, solutions, suspensions and the like. For parenternal administration the compounds may be combined with sterile aqueous or organic media to form injectable solutions or suspensions. The compounds may be administered to rectum as suppositories.

In man, the compounds of this invention may generally be administered in an amount of from about 5 mg/day to 2000 mg/day, preferably about 25 mg/day to 1000 mg/day, depending upon the symptom, the route of administration, and the particular compound of the invention. The present invention is illustrated by the following examples. However, it should be understood that the invention is not limited to the specific details of these examples.

REFERENCE EXAMPLE 1

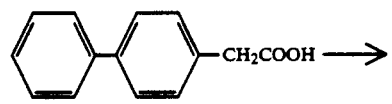

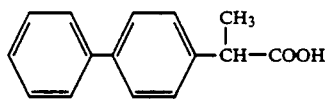

In usual manner, lithium diisopropylamide in tetrahydrofuran was prepared with diisopropylamine (3.2 ml, 22.6 mmol) and 1.6M n-butyllithium in hexane (14.2 ml, 22.6 mmol). ("Reagents for Organic Synthesis", 2, p. 249) To this lithium diisopropylamide in tetrahydrofuran was added dropwise 4-biphenylyl acetic acid (2.40 g, 11.3 mmol) in tetrahydrofuran at from −50° C. to −30° C. After the mixture was reacted at from −40° C. to −10° C. for 2 h, to the mixture was added dropwise methyliodide (1.77 g, 12.4 mmol) in tetrahydrofuran, then the temperature was rised at from −30° C. to room temperature in nature. After the mixture was stirred for 4 h, was added water and was adjusted at pH 2 with 3N sulfonic acid, then extracted with ether. After the ether extract was dried over, then the extract was evaporated under reduced pressure to a residue, which was chromatographed to afford 2-(4-biphenylyl)propionic acid (2.38 g, 93% yield) as white crystalline material: mp 144°–145° C.

REFERENCE EXAMPLE 2

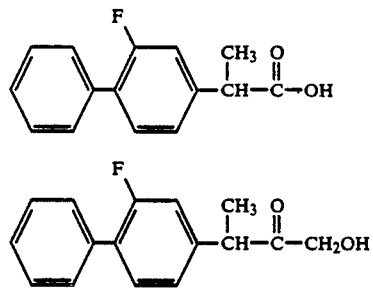

To thionyl chloride (40 ml) was added 2-(2-fluoro-4-biphenylyl) propionic acid (10.0 g, 40.9 mmol) by portions with stirring at room temperature. After the addition, the mixture was stirred over night at room temperature, and the solution was evaporated under reduced pressure to afford the acid chloride. After tris(trimethylsilyloxy)ethylene (35.9 g, 123 mmol) was added to the acid chloride at room temperature, the mixture was stirred at 95° C. for 4 h, then cooled to room temperature. After the addition of dioxane (53.5 ml) and then 0.6N hydrochloric acid (21.5 ml) dropwise to the mixture, the solution was stirred at 85° C. for 30 min, then cooled to room temperature, saturated with sodium chloride, and extracted with ether. The ether extracts were washed with water, dried with anhydrous sodium sulfate, and evaporated under reduced pressure to a residue, which was chromatographed to afford 3-(2-fluoro-4-biphenylyl)-2-oxo-1-butanol (10.0 g, 95% yield) as crystalline material: mp 63°–64.5° C.; NMR(CDCl$_3$)δ1.48(d, 3H), 2.97(t, 1H), 3.80(q, 1H), 4.25(d, 2H), 6.93–7.62(m, 8H) ppm; IR(neat) 3450, 1725, 1610, 1480, 1420, 1270 cm$^{-1}$.

According to substantially the same procedure as that of Reference Example 2, the following compounds were made.

TABLE 3

| Ref. Ex. No. | Structure | Physical Data |
|---|---|---|
| 3 | 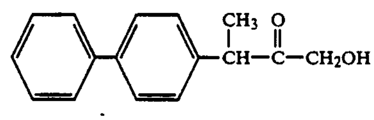 | mp. 87.5–89.0° C. |
| 4 | 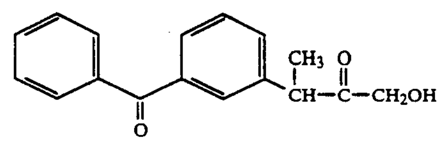 | NMR(CDCl$_3$)δ1.49(d, 3H) 2.97(t, 1H), 3.85(q, 1H), 4.20(d, 2H), 7.22–7.82 (m, 9H)ppm; IR(neat)3480, 1720, 1660, 1600, 1320, 1280 cm$^{-1}$ |

REFERENCE EXAMPLE 5

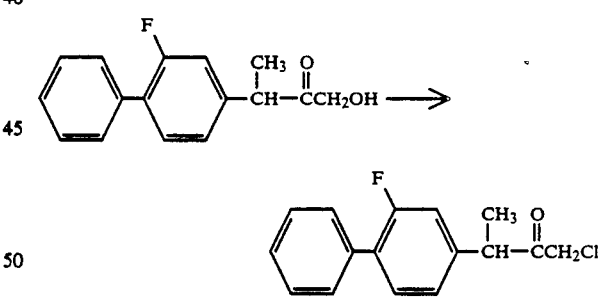

To 3-(2-fluoro-4-biphenylyl)-2-oxo-1-butanol (2.00 g, 7.74 mmol) in carbon tetrachloride (5 ml) was added triphenylphosphine (2.15 g, 8.20 mmol) at room temperature. After the addition, the mixture was stirred over night at room temperature, then concentrated to give triphenylphosphine oxide as precipitates. After filtration of the precipitates, the filtrates were evaporated under reduced pressure to a residue, which was chromatographed to afford 1-chloro-3-(2-fluoro-4-biphenylyl)-2-butanone (1.01 g, 47% yield) as crystalline materials: mp 57°–59° C.; NMR(CDCl$_3$)δ 1.48(d, 3H), 4.07(m, 3H), 6.93–7.63(m, 8H); IR(neat) 1740, 1620, 1480, 1420, 1270 cm$^{-1}$.

According to substantially the same procedure as that of Reference Example 5, the following compounds were made.

TABLE 4

| Ref. Ex. No. | Structure | Physical Data |
|---|---|---|
| 6 | 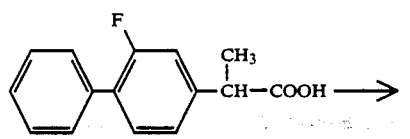 | mp. 101.0~102.5° C. |
| 7 | 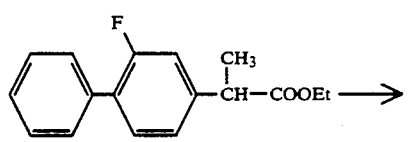 | NHR(CDCl₃)δ1.54(d, 3H), 4.06(s, 2H), 4.13(q, 1H), 7.30~7.90(m, 9H)ppm; IR(neat)1735, 1660, 1600, 1320, 1280 cm⁻¹ |

REFERENCE EXAMPLE 8

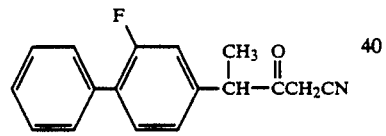

To 2-(2-fluoro-4-biphenylyl)-propionic acid (30.0 g, 0.123 mol) in ethanol (300 ml) was added conc. sulfonic acid (3.0 g). After the addition, the mixture was stirring at 50° C. for 5 h, then concentrated and extracted with benzene. The benzene extracts were washed with aqueous sodium hydrogen carbonate solution then with water, and dried over. The extracts were evaporated under reduced pressure to afford ethyl-2-(2-fluoro-4-biphenylyl)propionate (33.6 g, 0.123 mol) as oily residue.

After 60% sodium hydride (6.5 g, 0.163 mmol) was suspended in tetrahydrofuran under nitrogen atmosphere, the mixture was refluxed for 0.5 h, then added dropwise acetonitrile (7.6 g, 0.185 mol) and ethyl-2-(2-fluoro-4-biphenylyl)-propionate described above in tetrahydrofuran (100 ml). After refluxed for 2 h, the mixture was cooled at room temperature and added isopropylalcohol. After stirring for a while, the mixture was evaporated under reduced pressure to a residue, which was made acid with 2N hydrochloric acid and extracted with chloroform. The extracts were washed with water, dried over, and evaporated under reduced pressure to a residue, which was chromatographed and recrystallized with ethanol to afford 4-(2-fluoro-4-biphenylyl)-3-oxo-pentanenitril (18.0 g, 55% yield) as pale yellow crystalline material: mp 84°-85° C.

According to substantially the same procedure as that of Reference Example 8, the following compound was made.

TABLE 5

| Ref. Ex. No. | Structure | Physical Data |
|---|---|---|
| 9 | 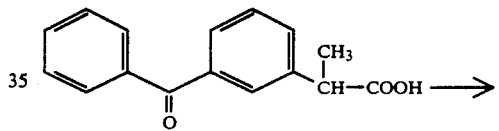 | NMR(CDCl₃)δ3,16(s, 2H), 3.91(s, 2H), 7.25~7.66 (m, 9H)ppm; IR(neat)2260, 1730, 1380, 1350, 1120 cm⁻¹ |

REFERENCE EXAMPLE 10

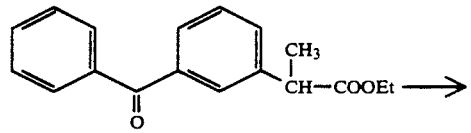

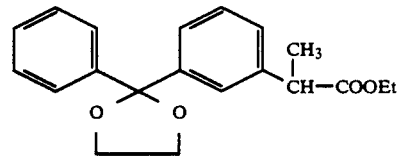

According to substantially the same procedure as that of Reference Example 8, ethyl 2-(3-benzoylphenyl) propionate (quantitative yield) was obtained from 2-(3-benzoylphenyl) propionic acid (30 g, 0.118 mol).

To ethyl 2-(3-benzoylphenyl) propionate in toluene (200 ml), was added ethylene glycol (20.0 g) and p-toluenesulfonic acid monoh-drate (1.0 g). After refluxed for 13 h, the mixture was cooled at room temperature and extracted with benzene. The extracts were washed with aqueous sodium hydrogen carbonate solution and then with water, and evaporated under reduced pressure to a residue, which was chromatographed to afford ethyl 2-(3-(2-phenyl-1,3-dioxolan -2-yl)phenyl) propionate (29.0 g, 75% yield) as oily residue: NMR(CDCl₃) δ 1.15 (t, 3H), 1.47(d, 3H), 3.68(q, 2H), 4.02(s, 4H), 4.07(q, 1H), 7.16-7.85(m, 9H) ppm; IR(neat) 3050, 1740, 1605, 1180, 1080 cm⁻¹.

REFERENCE EXAMPLE 11

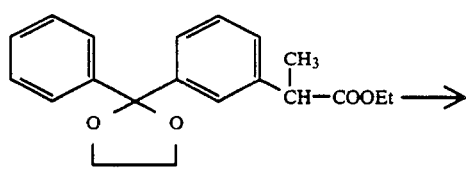

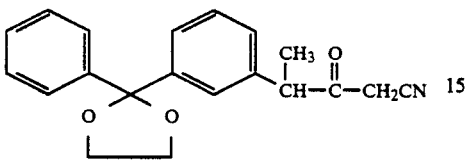

According to substantially the same procedure as that of Reference Example 8, with ethyl 2-(3-(2-phenyl-1,3-dioxolan-2-yl)phenyl)propionate 38.5 g, 118 mmol) was obtained 4-(3-(2-phenyl-1,3-dioxolan-2-yl)-phenyl)-3-oxo-pentanenitrile (12. 1 g, 38% yield) as pale yellow oily substance: NMR(CDCl$_3$) δ 1.41 (d, 3H), 3.28(s, 2H), 3.85(q, 1H), 4.03(s, 4H), 7.00–7.60(m. 9H) ppm; IR(neat) 2900, 2250, 1730, 1600, 1170, 1080 cm$^{-1}$.

REFERENCE EXAMPLE 12

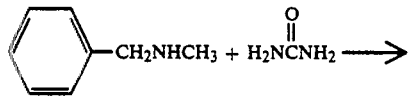

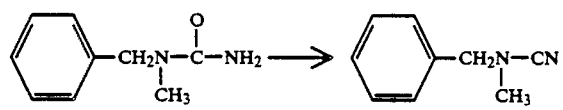

To N-methylbenzylamine (12.1 g, 0.1 mol) was added urea (6.0 g, 0.1 mol). After stirred at 118° C. for 4 h, the mixture was cooled to room temperature. The solidified mixture was ground to a powder, washed with n-hexane and recrystallized with ethyl acetate to afford N-methyl-N-benzylurea (12.3 g, 75% yield): mp 125°–129° C.

To N-methyl-N-benzylurea (1.64 g, 0.01 mol) in chloroform (24 ml) and 50% aqueous sodium hydroxide solution (5.4 ml) was added triethylamine (0.1 g, 0.001 mol) and the mixture was vigorously stirred at room temperature for 3.5 h. After addition of water and chloroform, the mixture was stirred, then extracted with chloroform. The extracts were washed with water, dried with anhydrous sodium sulfate, and evaporated under reduced pressure to a residue, which was chromatographed to afford N-methyl-N-benzylcyanamide (1.2 g, 82% yield) as oily substance: NMR(CDCl$_3$) δ 2.77(s, 3H), 4.14(s, 2H), 7.25–7.50(m, 5H); IR(neat) 2220, 1495, 1455, 1365, 730 cm$^{-1}$.

According to substantially the same procedure as that of Reference Example 12, the following compound was made.

TABLE 6

| Ref. Ex. No. | Structure | Physical Data |
|---|---|---|
| 13 | (pyrrolidine)N—CN | b.p. 80–84° C./10 mm Hg; NMR(CDCl$_3$)δ 1.91(t, 4H), 3.39(t, 4H)ppm; IR(neat) 2200, 1455, 1350 cm$^{-1}$ |

REFERENCE EXAMPLE 14

Ph–CH$_2$N(CH$_3$)—CN + HONH$_2$ →

Ph–CH$_2$N(CH$_3$)—C(=N—OH)—NH$_2$·HCl

To N-methyl-N-benzylcyanamide (10.6 g, 7.3 mmol) in ethanol (10 ml) was added hydroxylamine (0.528 g, 7.3 mmol). After reflux with stirring for 8 h, the mixture was evaporated under reduced pressure to a residue, which was recrystallized with mixture solution of isopropylalcohol and isopropylether to afford 1-methyl-1-benzyl-2-hydroxyguanidine hydrochloride (1.02 g, 65% yield) as crystalline material: mp 111°–114° C.

According to substantially the same procedure as that of Reference Example 14, the following compound was made.

TABLE 7

| Ref. Ex. No. | Structure | Physical Data |
|---|---|---|
| 15 | (CH$_3$)$_2$N—C(=N—OH)—NH$_2$·HCl | mp. 220° C. (decomposition) |

REFERENCE EXAMPLE 16

(biphenyl with F)—CH(CH$_3$)—COOH →

(biphenyl with F)—CH(CH$_3$)—C(=O)—CH$_2$Cl (+)-2-(2-Fluoro-4-biphenylyl)propionic acid (94.9% ee) was obtained by method of patent (Japan Kokai 53-112841). A solution of diazoketone in ether which was obtained by reaction of (+)-2-(2-fluoro-4-biphenylyl)propionic acid (200 mg, 0.82 mmol) obtained above with diazomethane by usual manner [W. E. Bachmann, W. S. Struve, Org. React., 1, 38 (1942)] was bubbled hydrogen chloride gas for 5 minute. The reaction mixture was washed with NaHCO$_3$ aq. and dried with magnesium sulfate. After evaporation, the residue was chromatographed to afford (+)-1-chloro-3-(2-fluoro-4-biphenylyl)-2-butanone (71.5 mg, 75% yield): (α)$_D^{25°}$ C·+180° (c=0.744, CHCl$_3$)

EXAMPLE 1

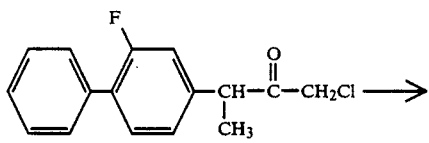

To thiourea (1.77 g, 23.3 mmol) in water (50 ml) was added 1-chloro-3-(2-fluoro-4-biphenylyl)-2-butanone (5.25 g, 19.0 mmol). After addition, the mixture was heated for 3 hr, and the solution was cooled to room temperature, then added 1N sodium hydroxide to pH 8. The mixture was extracted with chloroform and the chloroform extracts were washed with water, dried over, and evaporated under reduced pressure to a residue, which was chromatographed to afford 2-amino-4-[1-(2-fluoro-4-biphenylyl)ethyl] thiazole (4.12 g, 73% yield) as crystalline material: mp 167°–168° C.

EXAMPLE 2

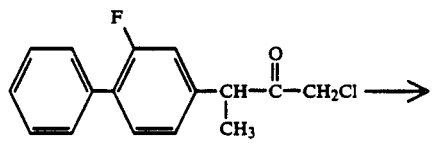

To N-methylthiourea (5.55 g, 61.6 mmol) in water was heated with 1-chloro-3-(2-fluoro-4-biphenylyl)-2-butanone (16.50 g, 59.6 mmol) at 90° C. for 3 hr. Treatment in same manner of Example 1 to give 4-[1-(2-fluoro-4-biphenylyl)ethyl]-2-methylaminothiazole (13.15 g, 71% yield): mp 129°–129.5° C.

According to substantially the same procedure as that of Example 1, there were obtained the thiazole derivatives of the formular (IV) as listed in Table 8.

TABLE 8

| Example | Structure | Physical Data |
|---|---|---|
| 3 | 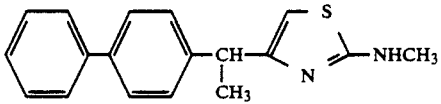 | 123.0–124.5° C. |
| 4 | 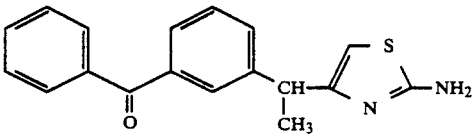 | 136–137° C. |
| 5 | 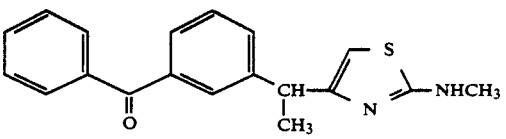 | 121–122° C. |
| 6 | 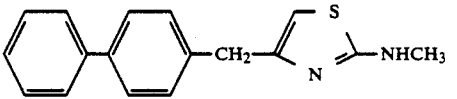 | 163.0° C. |

EXAMPLE 7

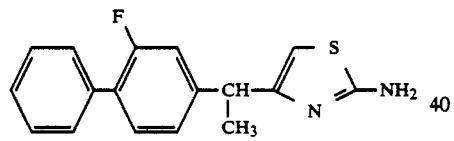

To 3-(2-Fluoro-4-biphenylyl)-2-oxo-1-butanol (3.57 g, 13.8 mmol) in tetrahydrofuran (35 ml) was added cyanamide (3.65 g, 77.6 mmol) in water and 2N-sodium hydroxide to pH 10. After the addition, the mixture was stirred overnight, then cyanamide (3.65 g, 77.6 mmol) was added to the reaction mixture to pH 10, the mixture was stirred overnight. The reaction mixture was extracted with ether and the extracts were washed with water, dried over and evaporated under reduced pressure to a residue, which was chromatographed to afford 2-Amino-4-(1-(2-fluoro-4-biphenylyl)ethyl)oxazole as crystalline material (1.05 g, 27% yield): mp 150.5°–151.5° C.

EXAMPLE 8

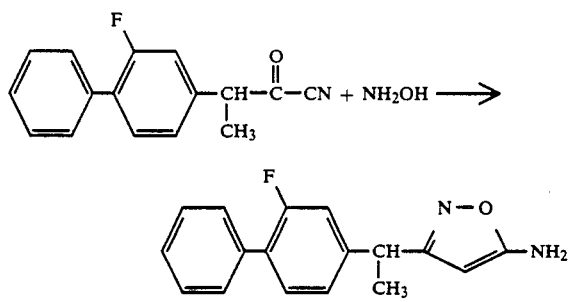

To 4-(2-Fluoro-4-biphenylyl)-3-oxo-pentanenitrile (2.75 g, 10.3 mmol) in ethanol (70 ml) was added hydroxylamine hydrochloride (1.1 g, 15.8 mmol) in pyridine (10 ml). After addition, the mixture was stirred at room temperature overnight, then evaporated under reduced pressure to a residue, which was chromatographed and then recrystalyzed to afford 5-amino-3-(1-(2-fluoro-4-biphenylyl)ethyl)isoxazole (2.20 g, 76% yield) as crystalline material: mp 122°-123° C.

According to substantially the same procedure as that of Example 8, there were obtained the isoxazole derivatives of the formula (VIII) as listed in Table 9.

To the mixture of 2-(3-benzoylphenyl) propionoic acid (3.00 g, 11.8 mmol), 1,1-dimethylamino-2-hydroxyguanidine hydrochloride (1.98 g, 14.2 mmol), N-hydroxybenztriazole (1.91 g, 14.2 mmol) and dicyclohexylcarbodiimide (2.92 g, 14.2 mmol) in N,N-dimethylformamide (100 ml) were added triethylamine (1.43 g, 14.2 mmol). After the addition, the mixture was stirred at room temperature for 12 hr, then filterated. The filterates were evaporated under reduced pressure to a residue, which was chlomatographed to afford 3-dimethylamino-5-(1-(3-benzoylphenyl)ethyl)-1,2,4-oxadiazole (2.00 g, 53% yield); NMR(CDCl$_3$) δ 1.27(d, 3H), 3.00(s, 6H), 4.32(q, 1H), 7.30-7.99(m, 9H) ppm; IR(neat) 1660, 1595, 1400, 1280 cm$^{-1}$.

TABLE 9

| Example | Structure | Physical Data |
|---|---|---|
| 9 | ![structure] | 138.5-139.0° C. |
| 10 | ![structure] | 145.5-146.0° C. |

EXAMPLE 11

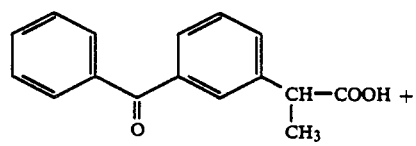

According to substantially the same procedure as that of Example 10, there were obtained the oxadiazole derivatives of the formula (XI) as listed in Table 10.

TABLE 10

| Example | Structure | Physical Data |
|---|---|---|
| 12 | ![structure] | NMR(CDCl$_3$)δ 3.00(s, 6H), 4.13(s, 2H), 7.33-7.93 (m, 9H)ppm; IR(neat)1660, 1600, 1400, 1280 cm$^{-1}$ |
| 13 | ![structure] | mp 65-67° C. |

TABLE 10-continued

| Example | Structure | Physical Data |
|---|---|---|
| 14 | 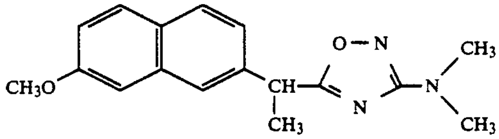 | mp 60-61° C. |
| 15 | 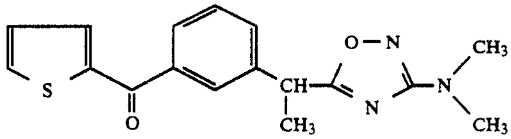 | mp 109.5-110.5° C. |
| 16 | 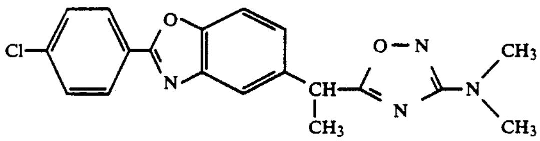 | mp 128.0-128.5° C. |
| 17 | 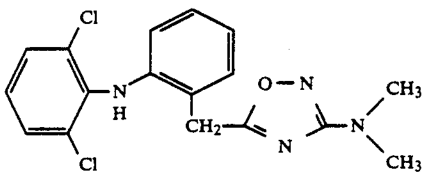 | mp 114.0-114.5° C. |
| 18 | 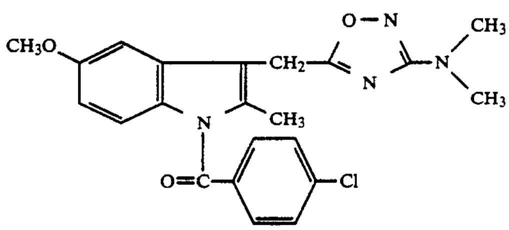 | mp 116.5-117.0° C. |
| 19 | 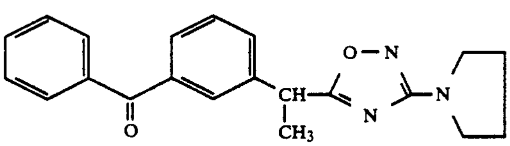 | NMR(CDCl₃)δ 1.72(d, 3H), 1.94(m, 4H), 3.41(m, 4H) 4.34(q, 1H), 7.30-8.11 (m, 9H)ppm; IR(neat)1660, 1595, 1410, 1285 cm⁻¹ |
| 20 | 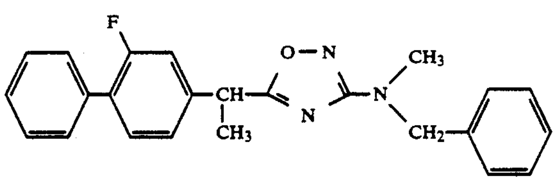 | NMR(CDCl₃)δ 1.71(d, 3H), 2.93(s, 3H), 4.26(q, 1H), 4.57(s, 2H), 7.05-7.60 (m, 13H)ppm; IR(neat)1595, 1485, 1455, 1410, 1265 cm⁻¹ |

EXAMPLE 21

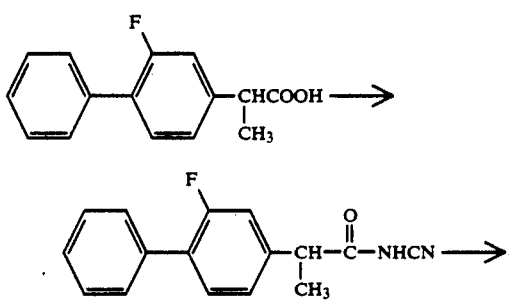

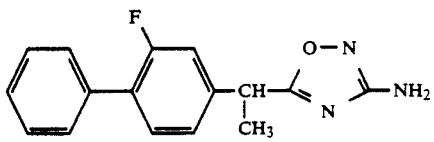

A mixture of 2-(2-fluoro-4-biphenylyl)propionic acid (5.00 g, 20.5 mmol) and thionyl chloride (10 ml) in benzene (50 ml) was stirred under reflux for 4 hr and the solution was evaporated under reduced pressure to afford the acid chloride. After the acid chloride was dissolved in acetone (15 ml), the solution was added to cyanamide (1.44 g, 30.8 mmol) in 2N-NaOH (16 ml) by portions at 0°-5° C. The mixture was controlled above pH 10 by 2N-NaOH during addition. After the addition, the mixture was stirred at room temperature for 15 hr, then diluted with water, acidified with 1N-HCl to pH 6 and extracted with ether. The water phase was acidified with 1N-HCl to pH 3 and then extracted with chloroform. The chloroform extracts were washed with saturated NaCl aq., dried with magnesium sulfate, then evaporated under reduced pressure to a residue, which was chlomatographed to afford N-(2-(2-fluoro-4-biphenylyl)propionyl)cyanamide. To hydroxylamine hydrochloride (2.20 g, 30.4 mmol) in pyridine (5 ml) was added N-(2-(2-fluoro-4-biphenylyl) propionyl)-cyanamide in ethanol (15 ml) by portion under cooling for 15 minute and the mixture was stirred at room temperature for 1 hr, then standed at room temperature overnight. To the reaction mixture was added 2N-NaOH (40 ml) to afford the precipitates. The precipitates were collected, washed with water, dried and recrystallized with ethyl acetate to afford 3-amino-5-(1-(2-fluoro-4-biphenylyl)ethyl)-1,2,4-oxadiazole (3.00 g, 52% yield): mp 174.5°-175.0° C.

According to substantially the same procedure as that of Example 21, there were obtained the oxadiazole derivatives of the formula (XIV) as listed in Table 11.

EXAMPLE 24

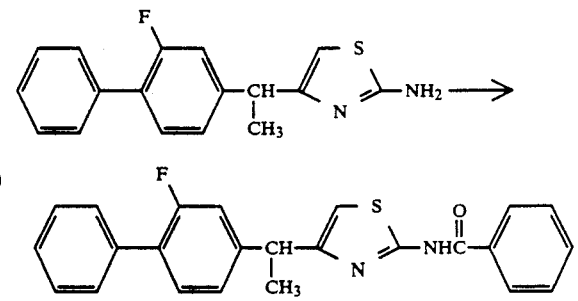

To 2-amino-4-(1-(2-fluoro-4-biphenylyl)ethyl)-thiazole (300 mg, 1.01 mmol) in tetrahydrofuran (15 ml) was added benzoyl chloride (145 mg, 1.03 mmol) and triethylamine (101 mg, 1.00 mmol) and the mixture was stirred at room temperature overnight. After reaction, the reaction mixture was filterated and evaporated under reduced pressure to a residue, which was cromatographed to afford 2-benzamido-4-(1-(2-fluoro-4-biphenylyl)ethyl)thiazole (279 mg, 69% yield): mp 147°-147.5° C.

According to substantially the same procedure as that of Example 24, there were obtained the azole derivatives of the formula (XVII) as listed in Table 12.

TABLE 11

| Example | Structure | Physical Data |
|---|---|---|
| 22 | ![structure] | mp 122.0–123.0° C. |
| 23 | ![structure] | mp 173.0–174.0° C. |

TABLE 12

| Example | Structure | Physical Data |
|---|---|---|
| 25 | ![structure] | mp 126.5–128.0° C. |
| 26 | ![structure] | mp 159.0–160.0° C. |
| 27 | ![structure] | mp 143.0–143.5° C. |

TABLE 12-continued

| Example | Structure | Physical Data |
|---------|-----------|---------------|
| 28 | 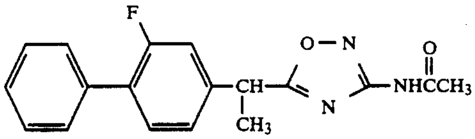 | mp 162.5–163.5° C. |
| 29 | 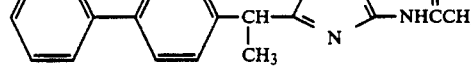 | NMR(CDCl₃)δ1.67(d, 3H), 3.09(t, 2H), 3.77(s, 3H), 3.89(t, 2H), 4.21(q, 1H), 6.65(s, 1H), 7.05–7.56 (m, 8H)ppm; IR(neat)1660, 1485, 1430, 1285, 1115, 755, 695 cm⁻¹ |

EXAMPLE 30

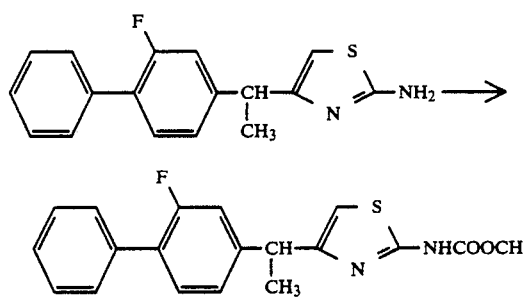

To 2-amino-4-(1-(2-fluoro-4-biphenylyl)ethyl)-thiazole (5.00 g, 1.68 mmol) in tetrahydrofuran (150 ml) was added ethyl chloroformate (1.82 g, 16.8 mmol) and triethylamine (1.70 g, 16.8 mmol) and the mixture was stirred under reflux for 2 hr. After cooling, the reaction mixture was diluted with water, then extracted with ethyl acetate. The extracts were washed with 1N-HCl and water, dried, then evaporated under reduced pressure to a residue, which was chromatographed to afford 2-ethoxycarbonylamino-4-(1-(2-fluoro-4-biphenylyl)ethyl) thiazole (3.954 g, 64% yield): NMR(CDCl₃)δ 1.31(t, 3H), 1.60(t, 3H), 4.25(m, 3H), 6.58(s, 1H), 6.95–7.58(m, 8H) ppm; IR(nujol) 3280, 1720, 1290, 1230, 1080 cm⁻¹.

According to substantially the same procedure as that of Example 30, there were obtained the azole derivatives of the formula (XVII) as listed in Table 13.

TABLE 13

| Example | Structure | Physical Data |
|---------|-----------|---------------|
| 31 | 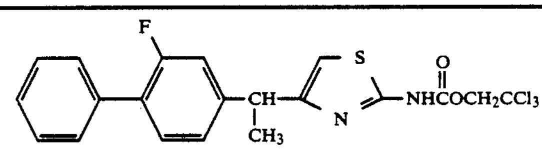 | NMR(CDCl₃)δ1.62(d, 3H), 4.20(q, 1H), 4.85(s, 2H), 6.60(s, 1H), 6.90–7.58 (m, 8H), 9.12(m, 1H)ppm IR(nujol)1750, 1560, 1380, 1280 cm⁻¹ |
| 32 | 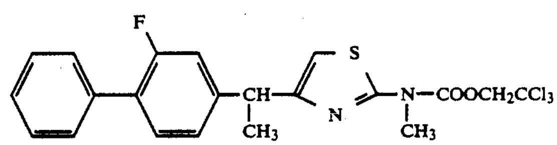 | mp. 104.0–105.0° C. |
| 33 | 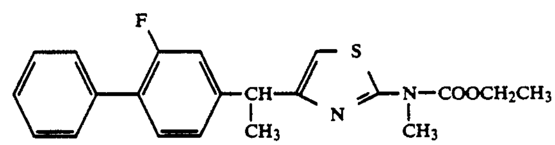 | mp 93.5–94.5° C. |
| 34 | 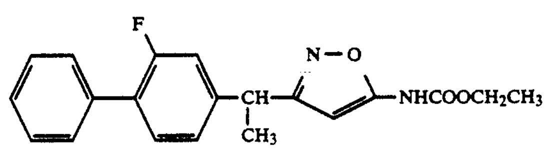 | NMR(CDCl₃)δ1.25(t, 3H), 1.71(d, 3H), 4.26(q, 3H), 5.98(s, 1H), 6.94–7.58(m, 8H)ppm; IR(neat)1810, 1775, 1620, 1240, 1100 cm⁻¹ |
| 35 | 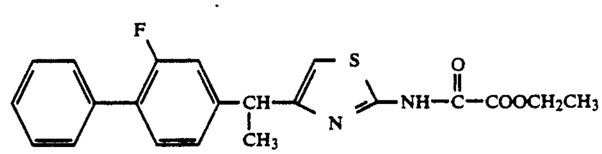 | mp 136.0–136.5° C. |

TABLE 13-continued

| Example | Structure | Physical Data |
|---|---|---|
| 36 | 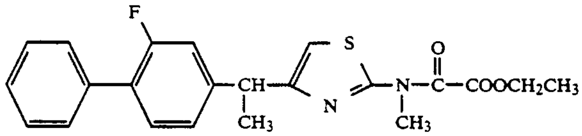 | NMR(CDCl₃)δ1.41(t, 3H), 1.68(d, 3H), 3.68(s, 3H), 4.24(q, 1H), 4.43(q, 2H), 6.73(s, 1H), 7.07-7.55 (m, 8H)ppm; IR(neat)1745, 1670, 1520, 1490, 1440, 1420, 1285, 1240, 1100, 1070, 760 cm⁻¹ |
| 37 | 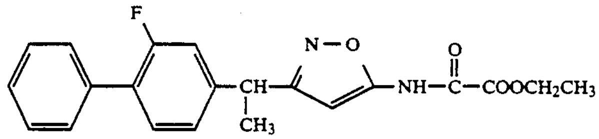 | mp 123.5-125.0° C. |
| 38 | 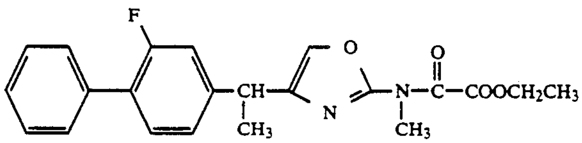 | NMR(CDCl₃)δ1.22(t, 3H), 1.58(d, 3H), 3.40(s, 3H), 4.15(q, 2H), 4.98(q, 1H), 7.02-7.55(m, 9H)ppm; IR(neat)1750, 1700, 1600, 1420, 1220, 1140 cm⁻¹ |

EXAMPLE 39

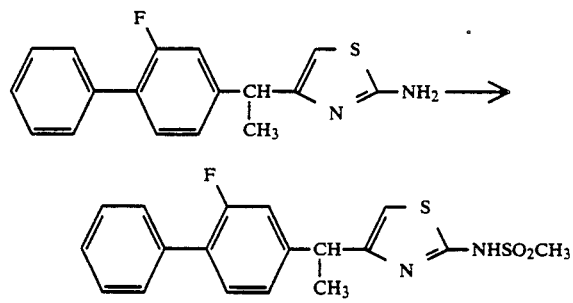

To a mixture of 2-amino-4-(1-(2-fluoro-4-biphenylyl)ethyl)thiazole (500 mg, 1.68 mmol) and triethylamine (340 mg, 3.36 mmol) in tetrahydrofuran was added methanesulfonyl chloride (385 mg, 3.36 mmol) by portion and the mixture was stirred at room temperature overnight. The reaction mixture was diluted with water, extracted with ethyl acetate and evaporated under reduced pressure to a residue, which was chromatographed and then recrystallized to afford 2-methanesulfonylamino-4-(1-(2-fluoro-4-biphenylyl)ethyl)thiazole (447 mg, 71% yield): mp 127.5°-129.0° C.

According to substantially the same procedure as that of Example 39, there were obtained the azole derivatives of the formula (XVII) as listed in Table 14.

TABLE 14

| Example | Structure | Physical Data |
|---|---|---|
| 40 | 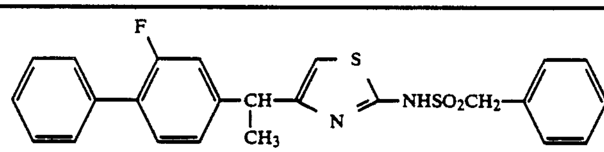 | mp 111.0-114.0° C. |
| 41 | 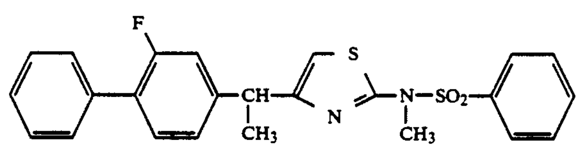 | mp 163.0-164.0° C. |
| 42 | 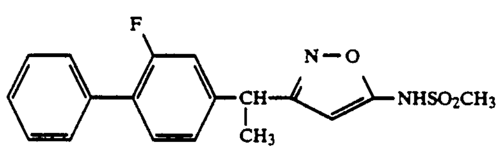 | mp 170.5-172.0° C. |
| 43 | 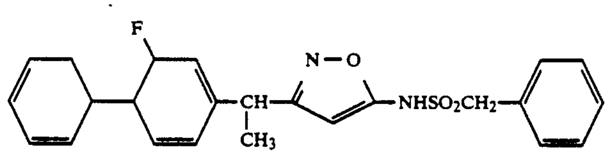 | NMR(CDCl₃)δ1.65(d, 3H), 4.12(q, 1H), 4.32(s, 2H), 5.45(s, 1H), 7.06-7.56 (m, 8H)ppm; IR(neat)1600, 1560, 1410, 1350 cm⁻¹ |

TABLE 14-continued

| Example | Structure | Physical Data |
|---|---|---|
| 44 | ![structure] | NMR(CDCl$_3$)δ1.67(d, 3H), 3.32(s, 3H), 4.18(q, 1H), 5.99(s, 1H), 6.99–7.74 (m, 8H)ppm; IR(neat)1590, 1480, 1420, 1365, 1175, 1070, 985, 835, 750, 725 cm$^{-1}$ |
| 45 | ![structure] | NMR(CDCl$_3$)δ1.59(d, 3H), 3.27(s, 3H), 3.41(s, 3H), 4.01(q, 1H), 7.05–7.55 (m, 9H)ppm; IR(neat)1590, 1360, 1160, 980, 880, 850 cm$^{-1}$ |
| 46 | ![structure] | NMR(CDCl$_3$)δ1.64(d, 3H), 2.97(s, 3H), 4.06(q, 1H), 4.73(q, 2H), 7.09–7.56 (m, 14H)ppm; IR(neat)1590, 1360, 1170, 970, 850 cm$^{-1}$ |

EXAMPLE 47

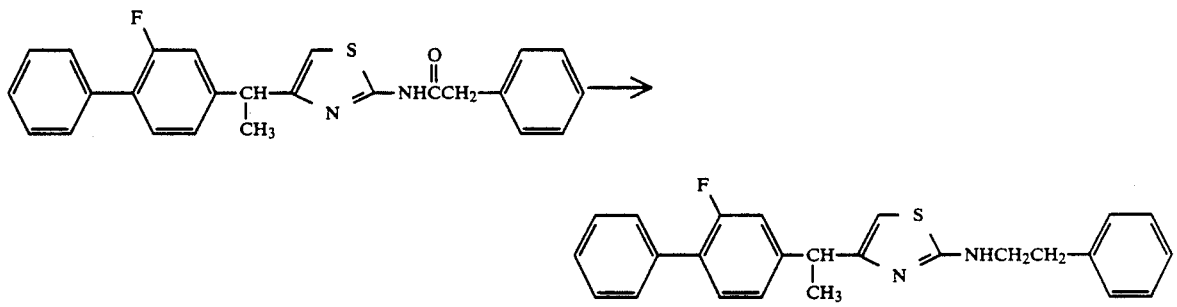

To 2-phenylacetamido-4-(1-(2-fluoro-4-biphenylyl)ethyl)thiazole (1.00 g, 2.51 mmol) in tetrahydrofuran (20 ml) was added lithium aluminu hydride (150 mg) by portion, then the mixture was refluxed for 2 hr. After cooling, the reaction mixture was filterated and evaporated under reduced pressure to a residue. The residue was extracted with chloroform and the extracts were washed with water, dried, then evaporated under reduced pressure to a residue, which chromatographed and recrystallized to afford 4-(1-(2-fluoro-4-biphenylyl)ethyl)-2-phenethylaminothiazole (504 mg, 50% yield): mp 74.5°–75.5° C.

EXAMPLE 48

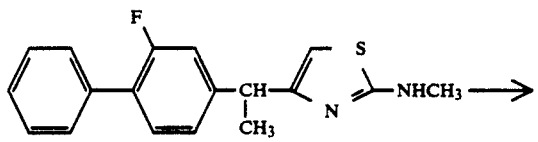

To 4-(1-(2-fluoro-4-biphenylyl)ethyl)-2-methylaminothiazole(415 mg, 1.33 mmol) in benzene (6 ml) was added methyl iodide (370 mg, 2.61 mmol), tetra-n-butyl ammonium hydrogene sulfate (435 mg, 1.33 mmol) and 50% NaOH aq. (3 ml), then the mixture was stirred at room temperature overnight. The reaction mixture was diluted with water, then acidified with 2N-HCl to pH 6 and the aqueous solution was extracted with benzene. The extracts were washed with water, dried and then evaporated under reduced pressure to a residue, which chromatographed to afford 4-(1-(2-fluoro-4-biphenylyl)ethyl)-2-dimethylaminothiazole (369 mg, 85% yield): NMR(CDCl$_3$)δ 1.62(d, 3H), 3.06(s, 6H), 4.09(q, 1H), 6.06(s, 1H), 7.02–7.63(m, 8H) ppm; IR(neat) 2950, 1620, 1550, 1420, 1340 cm$^{-1}$.

According to substantially the same procedure as that of Example 48, there were obtained the azole derivatives of the formula (XLV) as listed in Table 15.

TABLE 15

| Example | Structure | Physical Data |
|---|---|---|
| 49 | 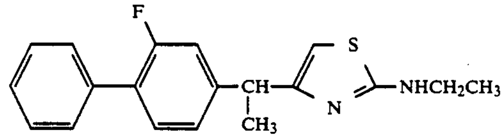 | mp 87.0–88.0° C. |
| 50 | 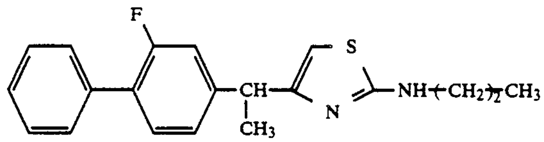 | NMR(CDCl₃)δ0.97(t, 3H), 1.60(d, 3H), 1.60–1.69 (m, 2H), 3.10–3.18(m, 2H), 4.06(q, 1H), 5.12–5.30(m, 1H), 6.15 (s, 1H), 7.02–7.54 (m, 8H)ppm; IR(neat)3200, 1620, 1340, 1260 cm⁻¹ |
| 51 | 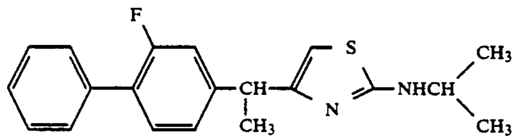 | NMR(CDCl₃)δ1.26(d, 6H), 1.60(d, 3H), 3.45–3.62 (m, 1H), 4.05(q, 1H), 5.50–5.80(m, 1H), 6.12(s, 1H), 7.03–7.54 (m, 8H)ppm; IR(nujol)3300, 1630, 1380, 1270 cm⁻¹ |
| 52 | 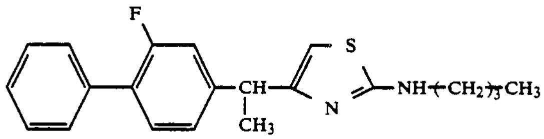 | NMR(CDCl₃)δ0.94(t, 3H), 1.33–1.47(m, 2H), 1.61(d, 3H), 1.56–1.66 (m, 2H), 3.16–3.21 (m, 2H), 4.06(q, 1H), 5.30–5.52(m, 1H), 6.15 (s, 1H), 7.03–7.54(m, 8H), ppm; IR(nujol)3400, 1600, 1380, 1340, 1270 cm⁻¹ |
| 53 | 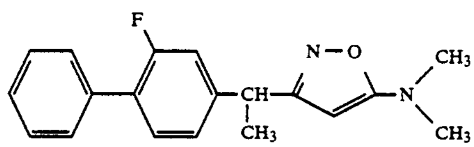 | mp 102.5–103.5° C. |
| 54 | 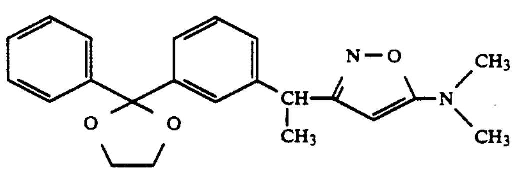 | NMR(CDCl₃)δ1.56(d, 3H), 3.77(s, 6H), 4.02(s, 4H), 4.03(q, 1H), 4.52(s, 1H), 7.15–7.60(m, 9H)ppm; IR(neat)2970, 1610, 1430, 1210 cm⁻¹ |
| 55 | 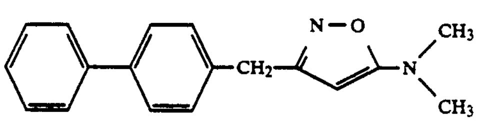 | mp 89.0–90.0° C. |

EXAMPLE 56

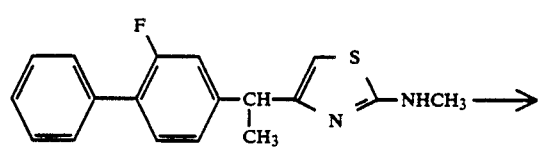

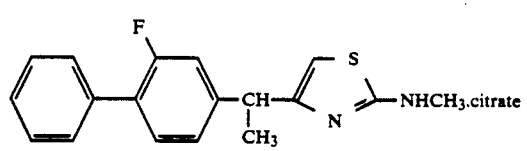

To 4-(1-(2-fluoro-4-biphenylyl)ethyl)-2-methylaminothiazole (200 mg, 0.64 mmol) in methanol was added citric acid (60 mg, 0.64 mmol) in methanol and the mixture was stirred at room temperature, then evaporated under reduced pressure to a residue, which was recrystallized to afford 4-(1-(2-fluoro-4-biphenylyl)ethyl)-2-methylamino-thiazole nitrate:mp 150°–151° C..

EXAMPLE 57

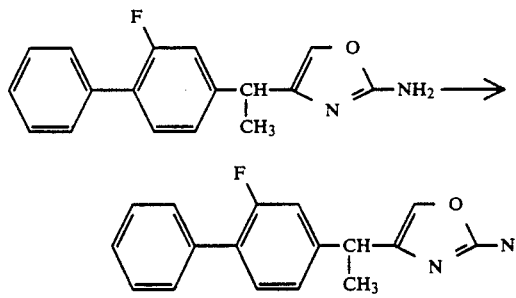

A mixture of 2-amino-4-(1-(2-fluoro-4-biphenylyl)ethyl)oxazole (1.66 g, 5.88 mmol) and ethyl orthoformate (20 ml) was refluxed for 5 hr and the reaction mixture was evaporated under reduced pressure to a residue. To the residue in ethanol (50 ml) was added sodium borohydride (0.27 g, 7.14 mmol) under cooling, then the mixture was stirred at room temperature for 2 hr. After evaporation, the residue was extracted with ethyl acetate and the extracts were washed with water, dried and then evaporated under reduced pressure to a residue, which was chromatographed and recrystallized to afford 4-(1-(2-fluoro-4-biphenylyl)ethyl)-2-methylaminooxazole (0.66 g, 40% yield): mp 133.5°-135.0° C.

According to substantially the same procedure as that of Example 57, there was obtained the azole derivative of the formula (XXIV) as listed in Table 16.

EXAMPLE 62

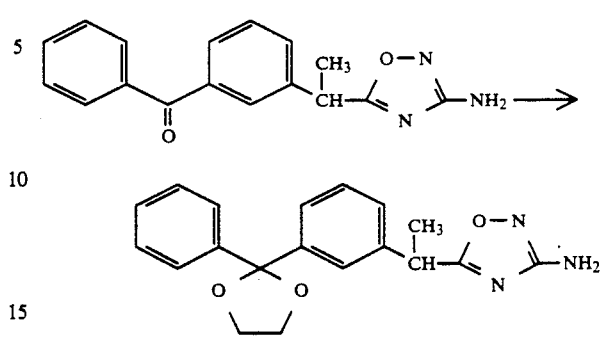

To 3-amino-5-(1-(3-benzoylphenyl)ethyl)-1,2,4-oxadiazole (1.20 g, 4.09 mmol) in toluene (10 ml) were added ethyleneglycol (0.80 g, 12.9 mmol) and p-toluenesulfonic acid monohydrate (0.025 g, 0.15 mmol). After reflux for 10 h, the mixture was cooled at room temperature and extracted with toluene. The extracts were washed with aqueous sodium hydrogen carbonate and then water, dried with anhydrous sodium sulfate, and evaporated under reduced pressure to a residue, which was chromatographed to afford 3-amino-5-(1-(3-(2-phenyl-1,3-dioxolan-2-yl)phenyl)ethyl)-1,2,4-oxadiazole (1.06 g, 77% yield) as crystalline material: mp 112.0°-113.5° C.

EXAMPLE 63

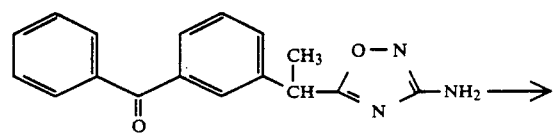

TABLE 16

| Example | Structure | Physical Data |
|---|---|---|
| 58 | 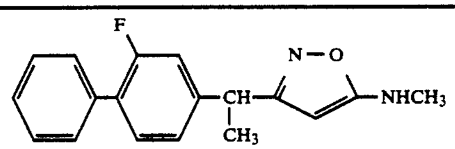 | mp 104.0–105.0° C. |
| 59 | 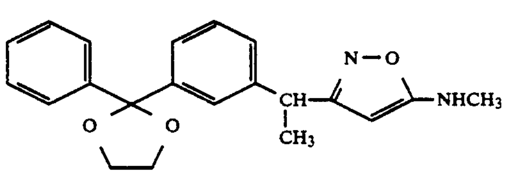 | NMR(CDCl₃) δ1.59(d, 3H), 2.85(d, 3H), 4.04(s, 4H), 4.05(q, 1H), 4.34(m, 1H), 4.63(s, 1H), 7.15–7.60 (m, 9H)ppm; IR(neat) 3300, 2980, 1620, 1420, 1215 cm⁻¹ |
| 60 | 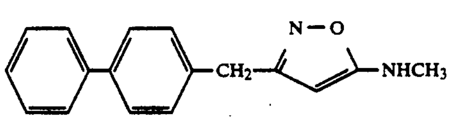 | mp 135.5–136.5° C. |
| 61 | 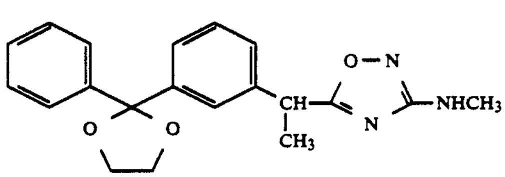 | NMR(CDCl₃) δ1.65(d, 3H), 2.88(d, 3H), 4.03(s, 4H), 4.20(q, 1H), 4.33(m, 1H), 7.16–7.60(m, 9H)ppm; IR(neat) 3330, 3000, 2900, 1610, 1460, 1220, 1180, 1090, 1080 cm⁻¹ |

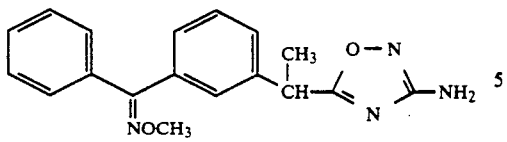

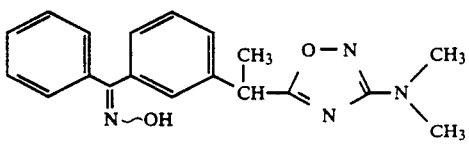

To 3-amino-5-(1-(3-benzoylphenyl)ethyl)-1,2,4-oxadiazole (0.60 g, 2.0 mmol) in pyridine (10 ml) was added methoxyamine hydrochloride (0.224 g, 2.7 mol). After reflux with stirring for 18 h, the mixture was poured upon ice water, extracted with ethylacetate. The extracts were washed with water, dried with anhydrous sodium sulfate, and evaporated under reduced pressure to a residue, which was chromatographed to afford 3-amino-5-(1-(3-(α-methoxyiminobenzyl)phenyl)ethyl)-1,2,4-oxadiazole (0.678 g, quantitive yield) as oily substance: NMR(CDCl$_3$)δ 1.70(d, 3H), 3.97(s, 3H), 4.24(q, 1H), 4.48(broad singlet, 2H), 7.21–7.58(m, 9H) ppm; IR(neat) 3310, 3220, 1625, 1585, 1410, 1050 cm$^{-1}$.

EXAMPLE 64

To 3-dimethylamino-5-(1-(3-benzoylphenyl)ethyl)-1,2,4-oxadiazole (1.0 g, 3.11 mmol) in ethanol (10 ml) were added hydroxylamine hydrochloride (0.25 g, 3.45 mmol) in water (2 ml) and sodium hydroxide (0.40 g, 9.5 mmol) in water (2 ml). After reflux with stirring for 24 h, the mixture was poured upon ice water and extracted with ethyl acetate. The ethyl acetate extracts were washed with saturated NaCl aq. dried with anhydrous magnesium salfate, and evaporated under redused pressure to a residue, which was chromatographed to afford 3-dimethylamino-5-(1-(3-(α-hydroxyiminobenzyl)phenyl)ethyl)-1,2,4-oxadiazole (0.873 g, 84% yield) as oily substance: NMR(CDCl$_3$)δ 1.66(d)+1.77(d) (3H), 2.98(s, 6H), 4.20(m, 1H), 7.22–7.55(m, 9H) ppm; IR(neat) 3700-3100, 1600, 1405 cm$^{-1}$.

According to substantially the same procedure as that of Example 64, the following compounds were made.

TABLE 17

| Example No. | Structure | Physical Data |
|---|---|---|
| 65 | (mixture of syn and anti) | NMR(CDCl$_3$) δ1.66(d) + 1.69(d) (3H), 4.12(q) + 4.26(q) (1H), 4.96(br) + 5.08(br) (2H), 7.16–7.73(m, 9H), 10.20 (br, 1H)ppm; IR(neat) 3325, 3200, 1630, 1460 cm$^{-1}$ |
| 66 | (mixture of syn and anti) | NMR(CDCl$_3$) δ1.62(d) + 1.72(d) (3H), 1.80~2.03 (m, 4H), 3.23-3.53 (m, 4H), 4.26(m, 1H), 7.17–7.53(m, 9H), 9.62(br, 1H)ppm; IR(neat) 3250, 1600, 1490, 1415, 1200 cm$^{-1}$ |
| 67 | (mixture of syn and anti) | NMR(CDCl$_3$) δ2.95 (s) + 2.97(s) (6H), 4.02(s) + 4.10(s) (2H), 7.24~7.52 (m, 9H), 9.68(br, 1H) ppm; IR (neat) 3250, 1600, 1400 cm$^{-1}$ |
| 68 | (mixture of syn and anti) | mp 189.0~190.0° C. |

EXAMPLE 69

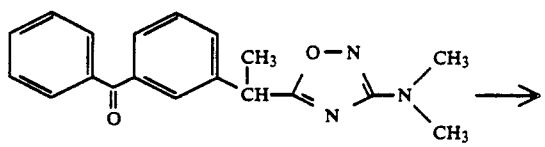

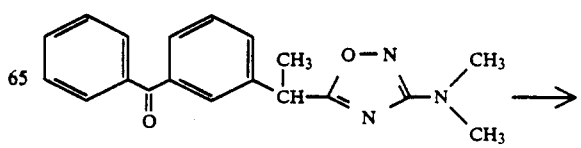

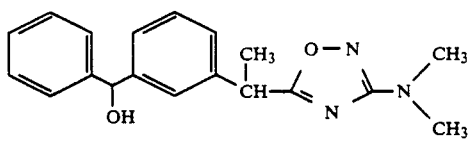

To sodium brohydride suspended (0.177 g, 4.7 mmol) in methanol (15 ml) under cooling with ice was slowly added dropwise 3-dimethylamino-5-(1-(3-benzoylphenyl) ethyl)-1,2,4-oxadiazole (1.45 g, 4.5 mmol) in methanol (15 ml). After the mixture was stirred under cooling with ice for 1 h, 1N-HCl was added to the mixture, then the mixture was adjusted at pH 6. The mixture was evaporated under reduced pressure to a residue, which was extracted with dichloromethane. The extracts were washed with saturated NaCl aq., dried with anhydrous magnesium sulfate, and evaporated under reduced pressure to a residue, which was chromatographed to afford 3-dimethylamino-5-(1-(3-(α-hydroxybenzyl)phenyl)ethyl-1,2,4-oxadiazole (1.50 g, 99% yield) as oily substance: NMR(CDCl$_3$)δ 1.45(d, 3H), 2.27(d, 1H), 3.00(s, 6H), 4.20(q, 1H), 5.80(d, 1H), 7.20-7.45(m, 9H) ppm; IR(-neat) 3375, 1600, 1405 cm$^{-1}$.

According to substantially the same procedure as that of Example 69, the following compound was made.

EXAMPLE 72

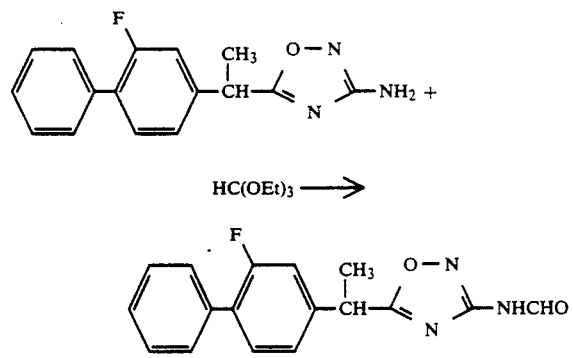

To triethyl orthoformate (6 ml) was added 3-amino-5-(2-(2-fluoro-4-biphenylyl)ethyl)-1,2,4-oxadiazole (0.10 g, 0.35 mmol). After the mixture was refluxed for 20 h, the mixture was evaporated under reduced pressure to a residue, which was extracted with chloroform after water was added. The extracts were dried with anhydrous potassium carbonate, and evaporated under reduced pressure to a residue, which was chromatographed to afford 3-formylamino-5-(2-(2-fluoro-4-biphenylyl)ethyl)-1,2,4-oxadiazole (0.091 g, 83% yield):

TABLE 18

| Example No. | Structure | Physical Data |
|---|---|---|
| 70 | 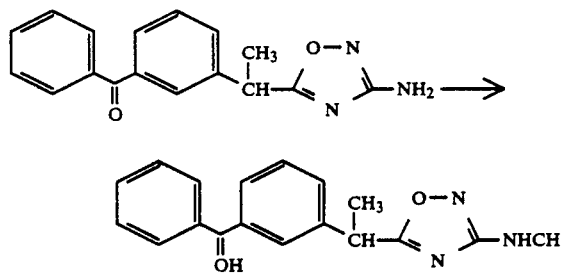 | NMR(CDCl$_3$) δ1.65(d, 3H), 2.96(br, 1H), 4.19(q, 1H), 4.50(br, 2H), 5.78(s, 1H), 7.15~7.48(m, 9H)ppm; IR(neat) 3500~3200, 1630, 1590, 1420 cm$^{-1}$ |

NMR(CDCl$_3$)δ 1.86(d, 3H), 4.40(q, 1H), 7.00-7.65(m, 8H), 9.06(broad, 2H) ppm; IR(nujol) 3275, 1740, 1580 cm$^{-1}$; mass m/e 311 (M+).

EXAMPLE 71

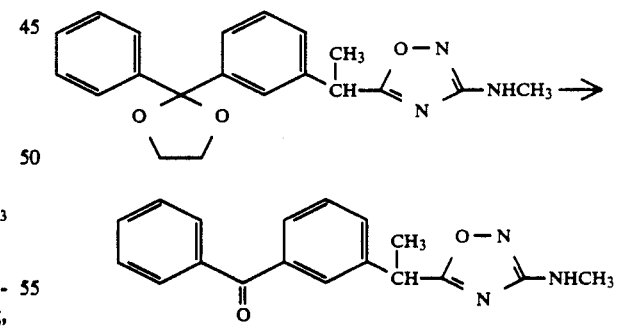

To triethyl orthoformate (10 ml) was added 3-amino-5-(1-(3-benzoylphenyl)ethyl)-1,2,4-oxadiazole (0.30 g, 1.02 mmol). After reflux for 4.5 h, the mixture was evaporated under reduced pressure to a residue, which was extracted with dichloromethane after saturated NaHCO$_3$ aq. was added. The extracts were washed with water, evaporated under reduced pressure to a residue, which was chromatographed to afford 3-methylamino-5-(1-(3-(α-hydroxybenzyl)phenyl)ethyl)-1,2,4-oxadiazole (0.15 g, 48% yield) as oily substance: NMR(CDCl$_3$)δ 1.63(d, 3H), 2.82(d, 4H), 4.18(q, 1H), 4.20(m, 1H), 5.73(d, 1H), 7.33-7.42(m, 9H) ppm; IR(-neat) 3430, 3330, 3040, 1600, 1490, 1450, 1340, 1320, 1150 cm$^{-1}$.

EXAMPLE 73

To the mixture of acetic acid (16 ml) and water (4 ml) was added 3-methylamino-5-(1-(3-(2-phenyl-1,3-dioxolan-2-yl)phenyl)ethyl)-1,2,4-oxadiazole (0.643 g, 2.44 mmol). After the mixture was stirred at room temperature overnight, the mixture was evaporated under reduced pressure to a residue, which was extracted with dichloromethane after saturated NaHCO$_3$ aq. was added. The extracts were washed with water, dried with anhydrous magnesium sulfate, and evaporated under reduced pressure to a residue, which was chromatographed and recrystallized with ethyl acetate and n-hexane to afford 3-methylamino-5-(1-(3-benzoyl-phenyl)ethyl)-1,2,4-oxadiazole (0.446 g, 59% yield) as crystalline material: mp 100°-101° C.

According to substantially the same procedure as that of Example 73, the following compounds were made.

-continued

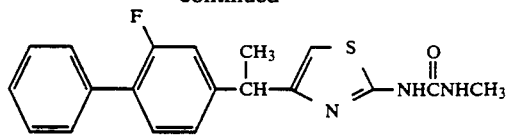

TABLE 19

| Example No. | Structure | Physical Data |
|---|---|---|
| 74 | (benzoyl-phenyl with CH(CH3) linked to isoxazole-NH2) | NMR(CDCl$_3$) δ1.60(d, 3H), 4.12(q, 1H), 4.40(m, 2H), 4.86(s, 1H), 7.23~7.85 (m, 9H)ppm; IR(neat) 3300, 3280, 1650, 1620, 1580, 1480, 1310 cm$^{-1}$ |
| 75 | (benzoyl-phenyl with CH(CH3) linked to isoxazole-NHCH3) | NMR(CDCl$_3$) δ1.63(d, 3H), 2.83(d, 3H), 4.13(q, 1H), 4.36(m, 1H), 4.70(s, 1H), 7.23~7.88(m, 9H)ppm; IR(neat) 3350, 2980, 1660, 1630, 1420, 1280 cm$^{-1}$ |
| 76 | (benzoyl-phenyl with CH(CH3) linked to isoxazole-N(CH3)2) | NMR(CDCl$_3$) δ1.63(d, 3H), 2.90(s, 6H), 4.13(q, 1H), 4.62(s, 1H), 7.23~7.88 (m, 9H)ppm; IR(neat) 2950, 1660, 1620, 1435, 1280 cm$^{-1}$ |

EXAMPLE 77

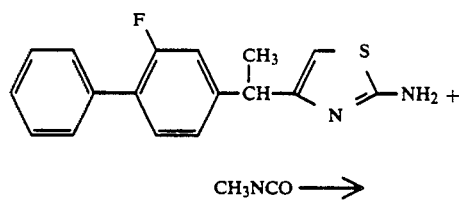

To 2-amino-4-(1-(2-fluoro-4-biphenylyl)ethyl) thiazole (500 mg, 1.68 mmol) in chloroform (20 ml) was added methylisocyanate (0.10 mg, 1.75 mmol) in chloroform (10 ml) under cooling with ice. After the mixture was stirred, methylisocyanate (0.15 mmol, 2.63 mmol) was added to the mixture, and then the mixture was stirred at room temperature overnight. The mixture was evaporated under reduced pressure to a residue, which was crystallized to afford N-methyl-N'-(4-(1-(2-fluoro-4-biphenylyl)ethyl) thiazol-2-yl)urea (0.499 g, 84% yield) as crystalline material: mp 208.5°-209.0° C.

According to substantially the same procedure as that of Example 77, the following compounds were made.

TABLE 20

| Example No. | Structure | Physical Data |
|---|---|---|
| 78 | (2-fluoro-biphenylyl-CH(CH3)-thiazole-N(CH3)-C(O)NHCH3) | NMR(CDCl$_3$) δ1.65(d, 3H), 2.87(d, 3H), 3.39(s, 3H), 4.13(q, 1H), 6.48(s, 1H), 7.04~7.56(m, 8H), 9.32 (m, 1H)ppm; IR(neat) 3200, 1670, 1410, 1320, 1100 cm$^{-1}$ |
| 79 | (2-fluoro-biphenylyl-CH(CH3)-thiazole-NHC(O)NH-phenyl) | mp 161.5~162.5° C. |
| 80 | (2-fluoro-biphenylyl-CH(CH3)-thiazole-N(CH3)-C(O)NH-phenyl) | mp 87.0~88.5° C. |

TABLE 20-continued

| Example No. | Structure | Physical Data |
|---|---|---|
| 81 | 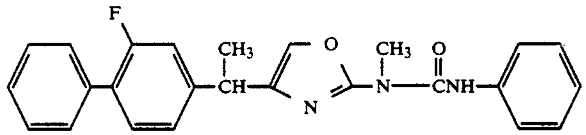 | mp 113.0~114.0° C. |

EXAMPLE 82

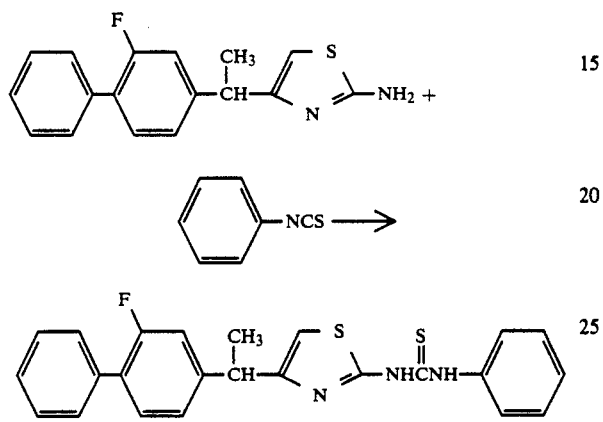

To 2-amino-4-(1-(2-fluoro-4-biphenylyl)ethyl) thiazole (0.50 g, 1.68 mmol) in acetone (10 ml) were added phenylisothiocyanate (0.25 g, 1.85 mmol) in acetone (5 ml) and sodium hydrogen carbonate (0.30 g). After the mixture was refluxed for 10 h, phenyisothiocyanate (0.50 g, 3.70 mmol) was added to the mixture, and then the mixture was refluxed for 2 h. The mixture was evaporated under reduced pressure to a residue, which was chromatographed and recrystallized to afford N-phenyl-N'-(4-(1-(2-fluoro-4-biphenylyl)ethyl)thiazol-2-yl)thiourea (0.115 g, 16% yield) as crystalline material: mp 176.5°-177.0° C.

According to substantially the same procedure as that of Example 82, the following compounds were made.

EXAMPLE 86

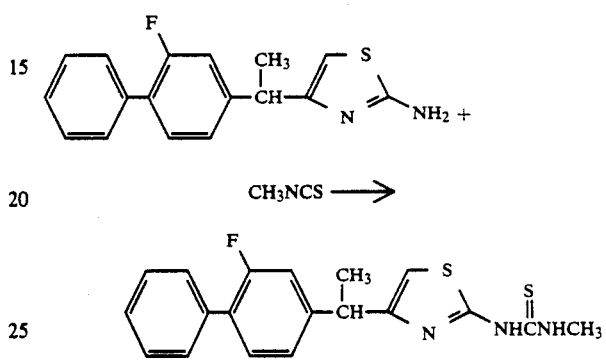

To lithium diisopropylamide in tetrahydrofuran prepared with diisopropylamine (0.187 g, 1.85 mmol) and n-butyllithium (1.9 mmol) was added 2-amino-4-(1-(2-fluoro-4-biphenylyl)ethyl)thiazole (0.50 g, 1.68 mmol) in tetrahydrofuran at −70° C. After the mixture was stirred for 20 min, methylisothiocyanate (0.131 g, 1.8 mmol) in tetrahydrofuran was added to the mixture. After the mixture was stirred at room temperature for 3.5 h, the mixture was evaporated under reduced pressure to a residue, which was extracted with chloroform. The extracts were washed with water, dried over, and evaporated under reduced pressure to a residue, which was chromatographed and recrystallized to afford N-methyl-N'-(4-(1-(2-fluoro-4-biphenylyl)ethyl)thiazol-2-yl)thiourea (0.233 g, 35% yield) as crystalline material: mp 180.5°-181.0° C.

According to substantially the same procedure as that of Example 86, the following compounds were made.

TABLE 21

| Example No. | Structure | Physical Data |
|---|---|---|
| 83 | 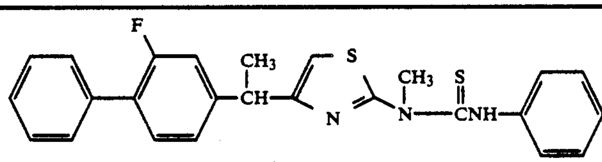 | NMR(CDCl$_3$) 1.65(d, 3H), 3.92(s, 3H), 4.15(q, 1H), 6.60(s, 1H), 6.95~7.60 (m, 13H)ppm; IR(neat)2930, 1560, 1490, 1300, 1180, 1060 cm$^{-1}$ |
| 84 | 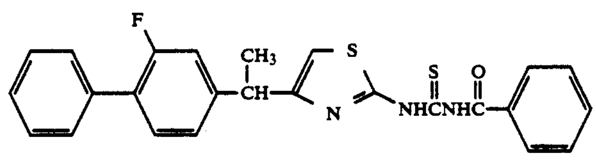 | mp 162.0~163.0° C. |
| 85 | 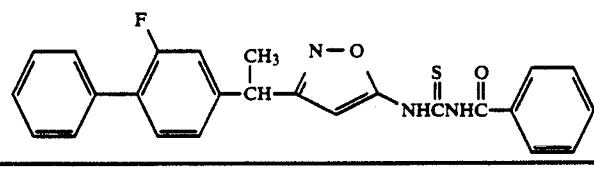 | mp 158.0~159.0° C. |

TABLE 22

| Example No. | Structure | Physical Data |
|---|---|---|
| 87 | 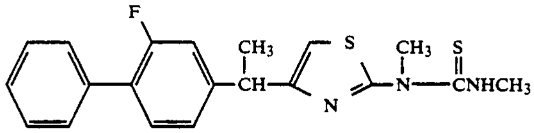 | NMR(CDCl₃) δ1.68(d, 3H), 3.15(d, 3H), 3.90(s, 3H), 4.17(q, 1H), 6.60(s, 1H), 6.97~7.6(m, 8H), 11.89 (br, 1H)ppm; IR(neat)3110, 1560, 1500, 1300, 1045 cm⁻¹ |
| 88 | 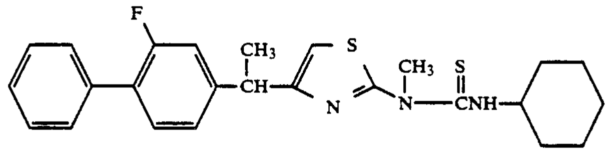 | NMR(CDCl₃) δ1.66(d, 3H), 0.80-2.20(m, 1H), 3.90 (s, 3H), 4.16(q, 1H), 6.65(s, 1H), 6.90-7.67 (m, 8H), 11.90(m, 1H) ppm; IR(neat)3150, 1560, 1500, 1335, 1315, 1075, 1040, 760 cm⁻¹ |
| 89 | 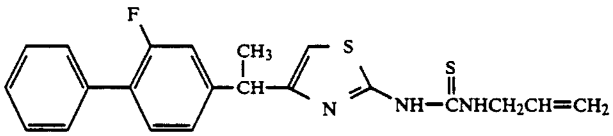 | mp 172.0–173.0° C. |
| 90 | 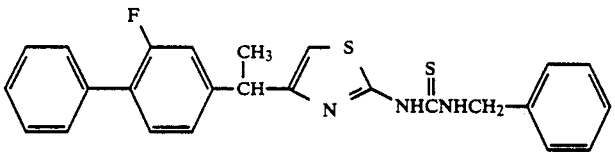 | mp 167.0–178.0° C. |

EXAMPLE 91

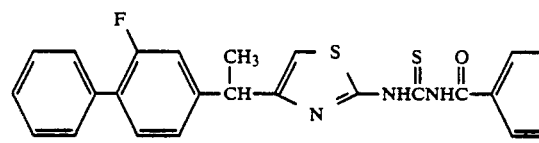

To N-benzoyl-N'-(4-(1-(2-fluoro-4-biphenylyl)ethyl)-thiazol-2-yl)thiourea (0.25 g, 0.561 mmol) in mixture of acetone (10 ml) and methanol (2.5 ml) was added potassium carbonate (0.05 g) in water (1 ml). After the mixture was refluxed for 5 h, the mixture was extracted with ethyl acetate. The extracts were washed with water, dried over, and evaporated under reduced pressure to residue, which was chromatographed and recrystallized with mixture of chloroform and n-hexane to afford N-(4-(1-(2-fluoro-4-biphenylyl)ethyl)thiazol-2-yl)thiourea (0.172 g, 82% yield) as crystalline material: 192.0°–194.0° C.

According to substantially the same procedure as that of Example 91, the following compound was made.

EXAMPLE 93

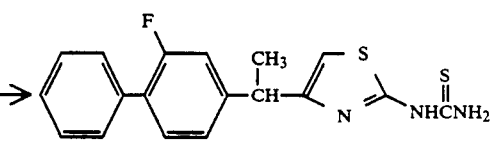

To 2-ethoxalylamino-4-(1-(2-fluoro-4-biphenylyl)ethyl)thiazole (0.50 g, 1.29 mmol) in ethanol (10 ml) was added ammonia water (2 ml). After the addition, the

TABLE 23

| Example No. | Structure | Physical Data |
|---|---|---|
| 92 | | mp 150.0–151.0° C. | mixture was refluxed for 2 h, evaporated under reduced pressure to a residue, which was extracted with chloroform. The extracts were dried over and evaporated under reduced pressure to residue, which was chromatographed to afford 2-oxamoylamino-4-(1-(2-fluoro-4-biphenylyl)ethyl)thiazole (0.121 g, 26% yield) as crystalline material: mp 179.0°-180.0° C.

According to substantially the same procedure as that of Example 93, the following compound was made.

6.70(s, 1H), 7.08-7.55(m, 8H)ppm; IR(neat) 2950, 1740, 1640, 1480, 1430, 1290, 1100 cm$^{-1}$.

According to substantially the same procedure as that of Example 95, the following compounds were made.

TABLE 25

| Example No. | Structure | Physical Data |
|---|---|---|
| 96 | 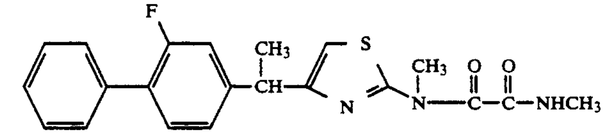 | mp 143.5-144.0° C. |
| 97 | 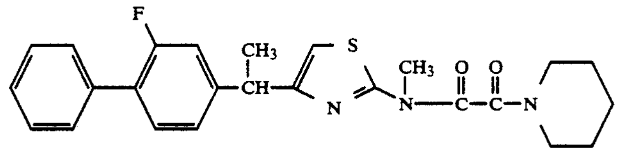 | NMR(CDCl$_3$) δ1.59-1.75 (m, 9H), 3.35(t, 2H), 3.63-3.67(m, 5H), 4.24(q, 1H), 6.70 (s, 1H), 7.07-7.56 (m, 8H)ppm; IR(neat)2940, 1740, 1650, 1480, 1430, 1280, 1260, 1100 cm$^{-1}$ |

EXAMPLE 98

TABLE 24

| Example No. | Structure | Physical Data |
|---|---|---|
| 94 | 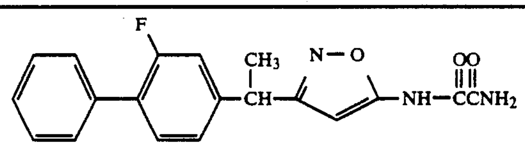 | mp 230.5° C. (decomposition) |

EXAMPLE 95

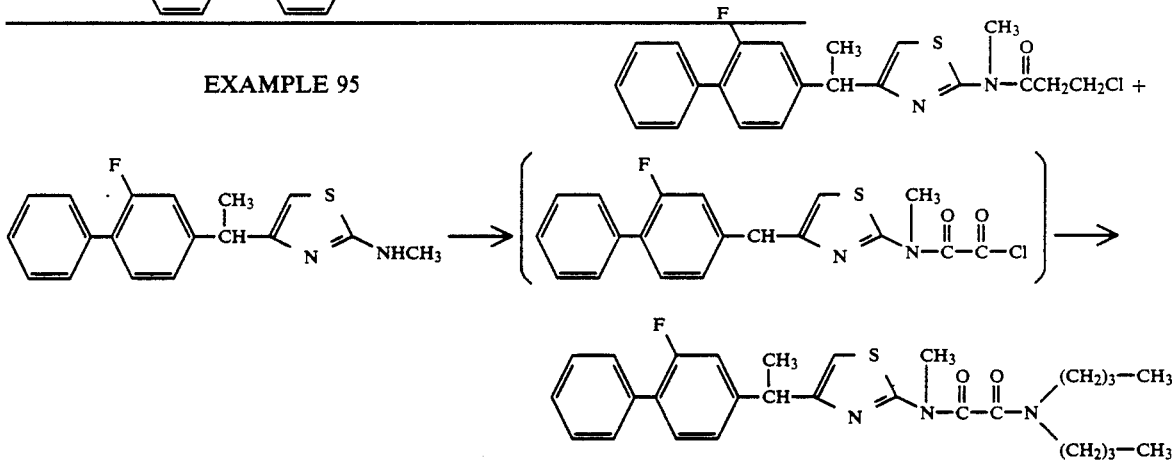

To oxalylchloride (1.22 g, 9.61 mmol) in tetrahydrofuran (20 ml) was added dropwise 4-(1-(2-fluoro-4-biphenylyl)ethyl)-2-methylthiazole (1.00 g, 3.20 mmol) in tetrahydrofuran (10 ml). After the addition, the mixture was stirred for 1 h at room temperature, then to the mixture was added dropwise di-n-butylamine (4.14 g, 32.0 mmol) in pyridine (5 ml) under cooling. After the addition, the mixture was stirred for 1 h at room temperature and extracted with ethyl acetate. The extracts were washed with water, dried over and evaporated under reduced pressure to a residue, which was chromatographed to afford N',N'-di-n-butyl-N-methyl-N-(4-(1-(2-fluoro-4-biphenylyl)ethyl)thiazole-2-yl)oxamide (142 mg, 9% yield) as oily substance: NMR(CDCl$_3$)δ 0.89(t, 3H), 0.97(t, 3H), 1.23-1.45(m, 4H), 1.55-1.70(m, 9H), 3.21(t, 2H), 3.45(t, 3H), 3.63(s, 3H), 4.25(q, 1H), To 2-(N-methyl-N-(3-chloropropionyl)amino-4-(1-(2-fluoro-4-biphenylyl)ethyl)thiazole (0.50 g, 1.24 mmol) in methanol (20 ml) was added ammonia water (5 ml). The mixture was refluxed for 5 h, and then evaporated under reduced pressure to a residue, which was extracted with ethyl acetate. The extracts were dried over and evaporated under reduced pressure to a residue, which was chromatographed and recrystallized with mixture of ethyl acetate and n-hexane to afford 2-(N-methyl-N-(3-aminopropionyl)amino-4-(1-(2-fluoro-4-biphenylyl)ethyl)thiazole (0.15 g, 39% yield) as crystalline material: mp 114.0°–117.0° C.

EXAMPLE 99

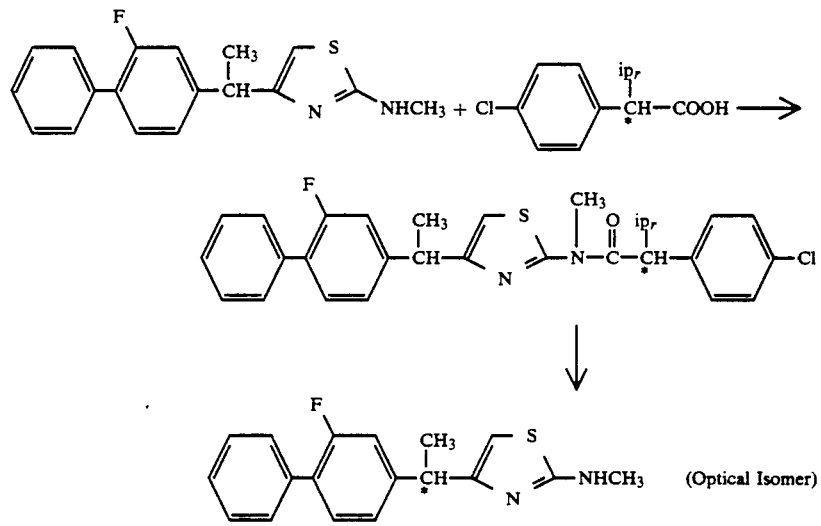

To 4-(1-(2-fluoro-4-biphenylyl)ethyl)-2-methylaminothiazole (16.0 g, 51.2 mmol) in dichloromethane (600 ml) were added 1-ethyl-3-(3-dimethylaminopropyl) carbodiimide hydrochloride (24.0 g, 0.125 mol), N-hydroxybenztriazole (10.7 g, 69.9 mmol), and (+)-2-p-chlorophenyl-3-methylbutyric acid (13.5 g, 63.5 mmol) under cooling with ice. The mixture was stirred at room temperature overnight, then washed with water, dried over, and evaporated under reduced pressure to a residue, which was chromatographed to afford two diastereomers (A & B) of 2-(N-methyl-N-(2-p-chlorophenyl-3-methyl-1-oxobutyl)amino-4-(1(2-fluoro-4-biphenylyl)ethyl)thiazole as crystalline materials.

TABLE 26

| Diastereomers | Yield | $[\alpha]_D^{25°C}$ (in CHCl₃) | Chemical Purity | mp |
|---|---|---|---|---|
| A | 3.73 g | +52.4° | 99.4% | 100.5~101.5° C. |
| B | 3.99 g | +31.8° | 99.4% | 143.0~143.5° C. |

To compound A of two diastereomers (2.50 g, 4.93 mmol) in ethanol (850 ml) was added sodium peroxide (1.92 g, 24.6 mmol). After the mixture was stirred at 50° C. for 2 h, ammonia water was added to the mixture. The mixture was evaporated under reduced pressure to a residue, which was extracted with chloroform. The extracts were dried over and evaporated under reduced pressure to a residue, which was chromatographed and recrystallized to afford (+)-4-(1-(2-fluoro-4-biphenylyl)ethyl)-2-methylaminothiazole (0.70 g, 45% yield) as crystalline material: mp 147.0°–148.0° C.; $[\alpha]_D^{25°C}$(in CHCl₃) +29.2°; 92.6% ee*.

According to substantially the same procedure as the above without recrystallization, with compound B of two diastereomers (2.50 g, 4.93 mmol) was made (−)-4-(1-(2-fluoro-4-biphenylyl)ethyl)-2-methylaminothiazole (0.90 g, 58% yield) as crystalline material: mp 143.5°–145.0° C.; $[\alpha]_D^{25°C}$(in CHCl₃) −21.5°; 88.8%ee*.

*; Each of enantiomer excess (ee%) was calcurated according to following method; the diastereomers were measured by HPLC which were derived from each of optical isomers according to the same procedure as the above.

EXAMPLE 100

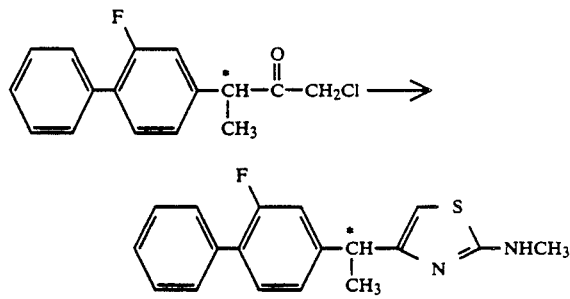

A mixture of (+)-1-chloro-3-(2-fluoro-4-biphenylyl)-2-butanone (27.7 mg, 0.1 mmol; $[\alpha]_D^{25°C}$+180° (c=0.744, CHCl₃), N-methylthiourea (9 mg, 0.1 mmol) and sodium bicarbonate (9.2 mg, 0.11 mmol) in methanol (1 ml) was stirred at room temperature for 28 hr and the mixture was diluted with NaCl aq., then extracted with ethyl acetate. The extracts were dried with magnesium sulfate and evaporated under reduced pressure to a residue, which was chromatographed to afford (+)-2-methylamino-4-(1-(2-fluoro-4-biphenylyl)ethyl)thiazole (21.9 mg, 70% yield): $[\alpha]_D^{25°C}$+10.7° (c=0.15, CHCl₃); 70%ee.

What is claimed is:
1. A compound of the formula:

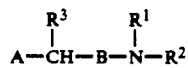

wherein A is the group of the formula:

wherein Ar$^1$ is phenyl or thienyl which may be optionally substituted with at least one of the same or different halogen; Ar$^2$ is phenylene or thienylene which may be optionally substituted with at least one of the same or different halogen; D is a divalent radical selected from the group consisting of >C=N—OR$^4$ wherein R$^4$ is hydrogen or lower alkyl, >C=O,

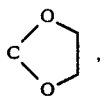

>CHOH, >NH and a single bond, or A is the group of the formula:

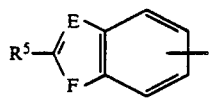

wherein R$^5$ is lower alkoxy or phenyl which may be optionally substituted with at least one of the same or different halogen; E is methine or nitrogen; F is vinylene or oxygen, or a is a group of the formula:

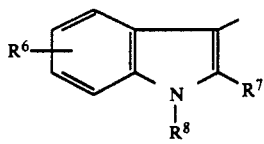

wherein R$^6$ is lower alkoxy; R$^7$ is lower alkyl; R$^8$ is benzoyl which may be optionally substituted with at least one of the same or different halogen, B is the divalent azole group, isoxazolediyl R$^1$ is hydrogen or lower alkyl; R$^2$ is hydrogen, lower alkyl, phenyllower alkyl, or the group of the formula:

R$^9$—G— wherein R$^9$ is hydrogen, lower alkyl, halo-lower alkyl, amino-lower alkyl, phenyl or phenyl-lower alkyl or the group of the formula:

wherein R$^{10}$ is hydrogen or lower alkyl; R$^{11}$ is hydrogen, lower alkyl, lower alkenyl, lower cycloalkyl, phenyl-lower alkyl, phenyl or aroyl, or the group of the formula: —NR$^{10}$R$^{11}$ which is pyrrolidinyl, piperidinyl or hexahydroazepinyl; or the group of the formula:

R$^{12}$—O— wherein R$^{12}$ is lower alkyl or polyhalo-lower alkyl; G is a divalent group selected from the group consisting of >C=O, >C=S, >(C=O)$_2$ and >SO$_2$ radical; and the group of the formula: —NR$^1$R$^2$ which is pyrrolidinyl, piperidinyl or hexahydroazepinyl; R$^3$ is hydrogen or lower alkyl, or its acid addition salts.

2. A compound of claim 1, wherein A is the group of the formula: Ar$^1$-D-Ar$^2$—.

3. A compound of claim 1, wherein A is the group of the formula: Ar$^1$-D-Ar$^2$— wherein Ar$^1$ is phenyl which may be optionally substituted with at least one of the same or different halogen; Ar$^2$ is phenylene which may be optionally substituted with at least one of the same or different halogen; D is carbonyl or a single bond; and R$^3$ is lower alkyl.

4. A compound of claim 3, wherein A is a group of the formula:

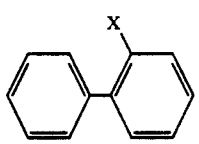

wherein X is hydrogen or halogen, or A is a group of the formula:

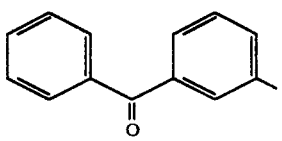

5. A compound of claim 3, wherein A is a group of the formula:

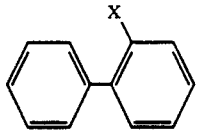

wherein X is hydrogen or halogen, or A is a group of the formula:

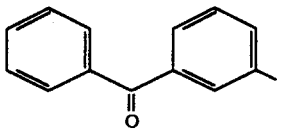

and R$^2$ is hydrogen or lower alkyl.

6. A pharmaceutical composition for treatment of autoimmune diseases, which comprises as active ingredient a pharmaceutically effective amount of at least one compound or its pharmaceutically acceptable acid addition salts as claimed in claim 1, and at least one pharmaceutically acceptable inert carrier or diluent.

7. A method for treatment of autoimmune diseases, which comprises administering to a person a pharmaceutically effective amount of at least one compound or its pharmaceutically acceptable acid addition salts as claimed in claim 1.

* * * * *